US008355766B2

(12) United States Patent
MacNeish, III et al.

(10) Patent No.: US 8,355,766 B2
(45) Date of Patent: Jan. 15, 2013

(54) CERAMIC EMITTER SUBSTRATE

(75) Inventors: William Jack MacNeish, III, Costa Mesa, CA (US); Mohamed K. Diab, Ladera Ranch, CA (US); David Dalke, Rancho Santa Margarita, CA (US)

(73) Assignee: Masimo Corporation, Irvine, CA (US)

( * ) Notice: Subject to any disclaimer, the term of this patent is extended or adjusted under 35 U.S.C. 154(b) by 1104 days.

(21) Appl. No.: 12/248,841

(22) Filed: Oct. 9, 2008

(65) Prior Publication Data
US 2009/0156913 A1 Jun. 18, 2009

Related U.S. Application Data

(60) Provisional application No. 60/998,659, filed on Oct. 12, 2007, provisional application No. 61/192,131, filed on Sep. 14, 2008.

(51) Int. Cl.
*A61B 5/00* (2006.01)

(52) U.S. Cl. .......................................... 600/310; 600/309

(58) Field of Classification Search .................. 600/309, 600/310, 322, 323, 331
See application file for complete search history.

(56) References Cited

U.S. PATENT DOCUMENTS

| | | | |
|---|---|---|---|
| 4,867,557 A * | 9/1989 | Takatani et al. .................. 356/41 |
| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Polczynski |
| 5,163,438 A | 11/1992 | Gordon et al. |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |

(Continued)

*Primary Examiner* — Jeffrey G Hoekstra
(74) *Attorney, Agent, or Firm* — Knobbe, Martens, Olson & Bear, LLP

(57) ABSTRACT

A ceramic emitter substrate has a substrate body with top and bottom sides and a cavity disposed on the top side. Bonding pads are disposed within the cavity and solder pads are disposed on the bottom side. Light emitting diodes (LEDs) are electrically connected to the bonding pads. Low-resistance conductors are disposed within the ceramic substrate body so as to interconnect the bonding pads and the solder pads. The interconnect is configured so that the LEDs can be individually activated as an array via row and column drive signals applied to the solder pads.

8 Claims, 26 Drawing Sheets

U.S. PATENT DOCUMENTS

| | | | |
|---|---|---|---|
| 5,758,644 | A | 6/1998 | Diab et al. |
| 5,760,910 | A | 6/1998 | Lepper, Jr. et al. |
| 5,769,785 | A | 6/1998 | Diab et al. |
| 5,782,757 | A | 7/1998 | Diab et al. |
| 5,785,659 | A | 7/1998 | Caro et al. |
| 5,791,347 | A | 8/1998 | Flaherty et al. |
| 5,810,734 | A | 9/1998 | Caro et al. |
| 5,823,950 | A | 10/1998 | Diab et al. |
| 5,830,131 | A | 11/1998 | Caro et al. |
| 5,833,618 | A | 11/1998 | Caro et al. |
| 5,860,919 | A | 1/1999 | Kiani-Azarbayjany et al. |
| 5,890,929 | A | 4/1999 | Mills et al. |
| 5,904,654 | A | 5/1999 | Wohltmann et al. |
| 5,919,134 | A | 7/1999 | Diab |
| 5,934,925 | A | 8/1999 | Tobler et al. |
| 5,940,182 | A | 8/1999 | Lepper, Jr. et al. |
| 5,995,855 | A | 11/1999 | Kiani et al. |
| 5,997,343 | A | 12/1999 | Mills et al. |
| 6,002,952 | A | 12/1999 | Diab et al. |
| 6,011,986 | A | 1/2000 | Diab et al. |
| 6,027,452 | A | 2/2000 | Flaherty et al. |
| 6,036,642 | A | 3/2000 | Diab et al. |
| 6,045,509 | A | 4/2000 | Caro et al. |
| 6,067,462 | A | 5/2000 | Diab et al. |
| 6,081,735 | A | 6/2000 | Diab et al. |
| 6,088,607 | A | 7/2000 | Diab et al. |
| 6,110,522 | A | 8/2000 | Lepper, Jr. et al. |
| 6,124,597 | A | 9/2000 | Shehada |
| 6,144,868 | A | 11/2000 | Parker |
| 6,151,516 | A | 11/2000 | Kiani-Azarbayjany et al. |
| 6,152,754 | A | 11/2000 | Gerhardt et al. |
| 6,157,850 | A | 12/2000 | Diab et al. |
| 6,165,005 | A | 12/2000 | Mills et al. |
| 6,184,521 | B1 | 2/2001 | Coffin, IV et al. |
| 6,206,830 | B1 | 3/2001 | Diab et al. |
| 6,229,856 | B1 | 5/2001 | Diab et al. |
| 6,232,609 | B1 | 5/2001 | Snyder et al. |
| 6,236,872 | B1 | 5/2001 | Diab et al. |
| 6,241,683 | B1 | 6/2001 | Macklem et al. |
| 6,256,523 | B1 | 7/2001 | Diab et al. |
| 6,263,222 | B1 | 7/2001 | Diab et al. |
| 6,278,522 | B1 | 8/2001 | Lepper, Jr. et al. |
| 6,280,213 | B1 | 8/2001 | Tobler et al. |
| 6,285,896 | B1 | 9/2001 | Tobler et al. |
| 6,321,100 | B1 | 11/2001 | Parker |
| 6,334,065 | B1 | 12/2001 | Al-Ali et al. |
| 6,343,224 | B1 | 1/2002 | Parker |
| 6,349,228 | B1 | 2/2002 | Kiani et al. |
| 6,360,114 | B1 | 3/2002 | Diab et al. |
| 6,368,283 | B1 | 4/2002 | Xu et al. |
| 6,371,921 | B1 | 4/2002 | Caro et al. |
| 6,377,829 | B1 | 4/2002 | Al-Ali |
| 6,388,240 | B2 | 5/2002 | Schulz et al. |
| 6,397,091 | B2 | 5/2002 | Diab et al. |
| 6,430,525 | B1 | 8/2002 | Weber et al. |
| 6,463,311 | B1 | 10/2002 | Diab |
| 6,470,199 | B1 | 10/2002 | Kopotic et al. |
| 6,501,975 | B2 | 12/2002 | Diab et al. |
| 6,505,059 | B1 | 1/2003 | Kollias et al. |
| 6,515,273 | B2 | 2/2003 | Al-Ali |
| 6,519,487 | B1 | 2/2003 | Parker |
| 6,525,386 | B1 | 2/2003 | Mills et al. |
| 6,526,300 | B1 | 2/2003 | Kiani et al. |
| 6,541,756 | B2 | 4/2003 | Schulz et al. |
| 6,542,764 | B1 | 4/2003 | Al-Ali et al. |
| 6,580,086 | B1 | 6/2003 | Schulz et al. |
| 6,584,336 | B1 | 6/2003 | Ali et al. |
| 6,595,316 | B2 | 7/2003 | Cybulski et al. |
| 6,597,932 | B2 | 7/2003 | Tian et al. |
| 6,597,933 | B2 | 7/2003 | Kiani et al. |
| 6,606,511 | B1 | 8/2003 | Ali et al. |
| 6,632,181 | B2 | 10/2003 | Flaherty et al. |
| 6,639,668 | B1 | 10/2003 | Trepagnier |
| 6,640,116 | B2 | 10/2003 | Diab |
| 6,643,530 | B2 | 11/2003 | Diab et al. |
| 6,650,917 | B2 | 11/2003 | Diab et al. |
| 6,654,624 | B2 | 11/2003 | Diab et al. |
| 6,658,276 | B2 | 12/2003 | Pishney et al. |
| 6,661,161 | B1 | 12/2003 | Lanzo et al. |
| 6,671,531 | B2 | 12/2003 | Al-Ali et al. |
| 6,678,543 | B2 | 1/2004 | Diab et al. |
| 6,684,090 | B2 | 1/2004 | Ali et al. |
| 6,684,091 | B2 | 1/2004 | Parker |
| 6,697,656 | B1 | 2/2004 | Al-Ali |
| 6,697,657 | B1 | 2/2004 | Shehada et al. |
| 6,697,658 | B2 | 2/2004 | Al-Ali |
| RE38,476 | E | 3/2004 | Diab et al. |
| 6,699,194 | B1 | 3/2004 | Diab et al. |
| 6,714,804 | B2 | 3/2004 | Al-Ali et al. |
| RE38,492 | E | 4/2004 | Diab et al. |
| 6,721,582 | B2 | 4/2004 | Trepagnier et al. |
| 6,721,585 | B1 | 4/2004 | Parker |
| 6,725,075 | B2 | 4/2004 | Al-Ali |
| 6,728,560 | B2 | 4/2004 | Kollias et al. |
| 6,735,459 | B2 | 5/2004 | Parker |
| 6,745,060 | B2 | 6/2004 | Diab et al. |
| 6,760,607 | B2 | 7/2004 | Al-All |
| 6,770,028 | B1 | 8/2004 | Ali et al. |
| 6,771,994 | B2 | 8/2004 | Kiani et al. |
| 6,792,300 | B1 | 9/2004 | Diab et al. |
| 6,813,511 | B2 | 11/2004 | Diab et al. |
| 6,816,741 | B2 | 11/2004 | Diab |
| 6,822,564 | B2 | 11/2004 | Al-Ali |
| 6,826,419 | B2 | 11/2004 | Diab et al. |
| 6,830,711 | B2 | 12/2004 | Mills et al. |
| 6,850,787 | B2 | 2/2005 | Weber et al. |
| 6,850,788 | B2 | 2/2005 | Al-Ali |
| 6,852,083 | B2 | 2/2005 | Caro et al. |
| 6,861,639 | B2 | 3/2005 | Al-Ali |
| 6,898,452 | B2 | 5/2005 | Al-Ali et al. |
| 6,920,345 | B2 | 7/2005 | Al-Ali et al. |
| 6,931,268 | B1 | 8/2005 | Kiani-Azarbayjany et al. |
| 6,934,570 | B2 | 8/2005 | Kiani et al. |
| 6,939,305 | B2 | 9/2005 | Flaherty et al. |
| 6,943,348 | B1 | 9/2005 | Coffin, IV |
| 6,950,687 | B2 | 9/2005 | Al-Ali |
| 6,961,598 | B2 | 11/2005 | Diab |
| 6,970,792 | B1 | 11/2005 | Diab |
| 6,979,812 | B2 | 12/2005 | Al-Ali |
| 6,985,764 | B2 | 1/2006 | Mason et al. |
| 6,993,371 | B2 | 1/2006 | Kiani et al. |
| 6,996,427 | B2 | 2/2006 | Ali et al. |
| 6,999,904 | B2 | 2/2006 | Weber et al. |
| 7,003,338 | B2 | 2/2006 | Weber et al. |
| 7,003,339 | B2 | 2/2006 | Diab et al. |
| 7,015,451 | B2 | 3/2006 | Dalke et al. |
| 7,024,233 | B2 | 4/2006 | Ali et al. |
| 7,027,849 | B2 | 4/2006 | Al-Ali |
| 7,030,749 | B2 | 4/2006 | Al-Ali |
| 7,039,449 | B2 | 5/2006 | Al-Ali |
| 7,041,060 | B2 | 5/2006 | Flaherty et al. |
| 7,044,918 | B2 | 5/2006 | Diab |
| 7,067,893 | B2 | 6/2006 | Mills et al. |
| 7,096,052 | B2 | 8/2006 | Mason et al. |
| 7,096,054 | B2 | 8/2006 | Abdul-Hafiz et al. |
| 7,132,641 | B2 | 11/2006 | Schulz et al. |
| 7,142,901 | B2 | 11/2006 | Kiani et al. |
| 7,149,561 | B2 | 12/2006 | Diab |
| 7,186,966 | B2 | 3/2007 | Al-Ali |
| 7,190,261 | B2 | 3/2007 | Al-Ali |
| 7,215,984 | B2 | 5/2007 | Diab |
| 7,215,986 | B2 | 5/2007 | Diab |
| 7,221,971 | B2 | 5/2007 | Diab |
| 7,225,006 | B2 | 5/2007 | Al-Ali et al. |
| 7,225,007 | B2 | 5/2007 | Al-Ali |
| RE39,672 | E | 6/2007 | Shehada et al. |
| 7,239,905 | B2 | 7/2007 | Kiani-Azarbayjany et al. |
| 7,245,953 | B1 | 7/2007 | Parker |
| 7,254,431 | B2 | 8/2007 | Al-Ali |
| 7,254,433 | B2 | 8/2007 | Diab et al. |
| 7,254,434 | B2 | 8/2007 | Schulz et al. |
| 7,272,425 | B2 | 9/2007 | Al-Ali |
| 7,274,955 | B2 | 9/2007 | Kiani et al. |
| D554,263 | S | 10/2007 | Al-Ali |
| 7,280,858 | B2 | 10/2007 | Al-Ali et al. |
| 7,289,835 | B2 | 10/2007 | Mansfield et al. |
| 7,292,883 | B2 | 11/2007 | De Felice et al. |

| | | |
|---|---|---|
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 2006/0211922 A1* | 9/2006 | Al-Ali et al. .......... 600/310 |

* cited by examiner

FIG. 8 LAYER-1

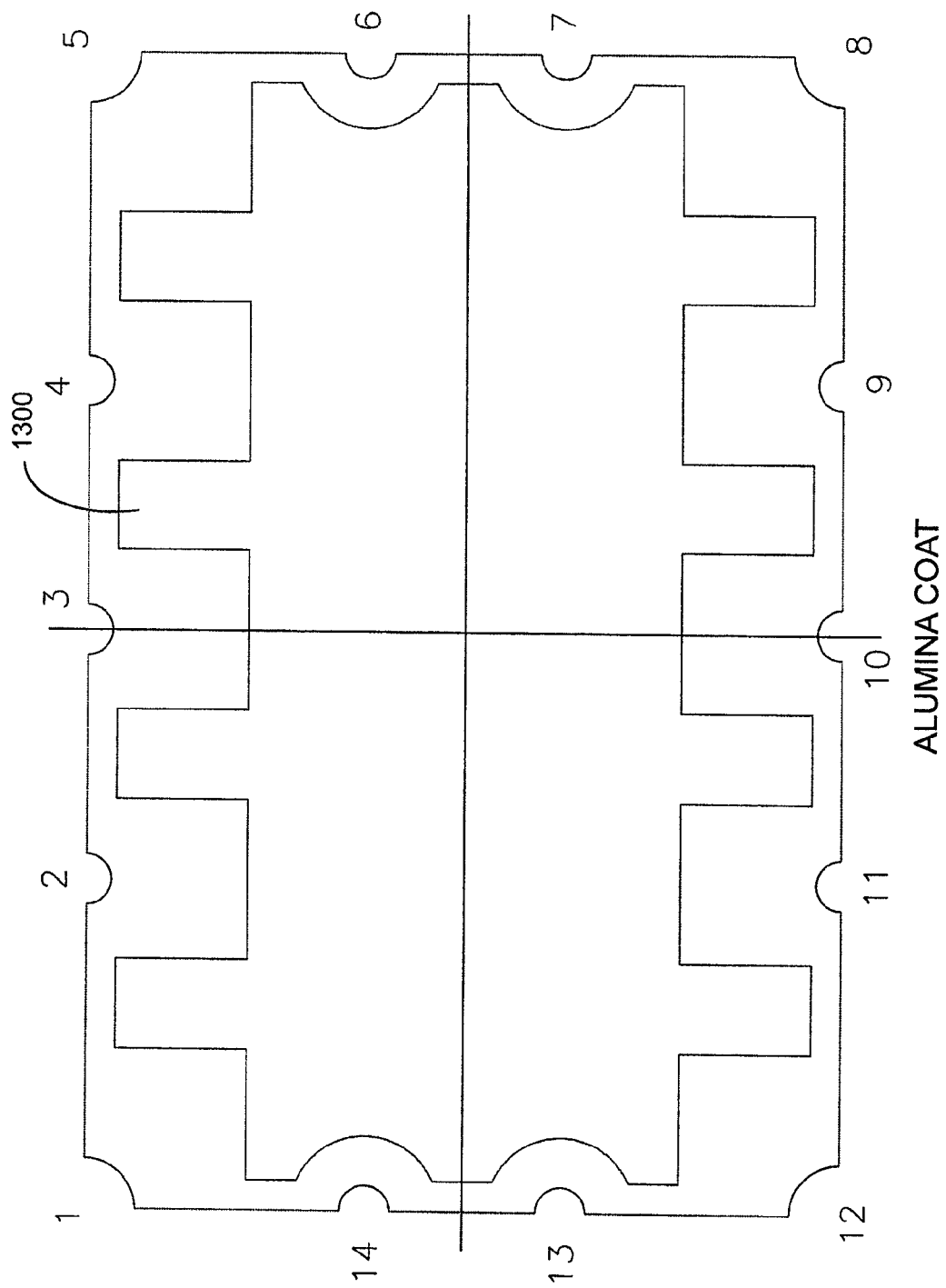

| Top Pad No. | Bottom Pad No. | Au Plating Surface | | Trace | Via | Total [mOHM] |
|---|---|---|---|---|---|---|
| | | Top | Bottom | | | |
| 1 | 10 | 12 | 6 | 276 | - | 294 |
| 7 | 10 | 12 | 6 | 108 | - | 126 |
| 11 | 10 | 12 | 6 | 96 | - | 114 |
| 2 | 1 | 24 | 6 | 74 | 22 | 126 |
| 6 | 1 | 24 | 6 | 204 | 22 | 256 |
| 12 | 1 | 6 | 6 | 216 | 10 | 238 |
| 3 | 12 | 24 | 6 | 120 | 12 | 162 |
| 5 | 12 | 24 | 6 | 84 | 12 | 126 |
| 13 | 12 | 6 | 6 | 96 | 10 | 118 |
| 4 | 3 | 12 | 6 | 192 | 22 | 232 |
| 10 | 3 | 12 | 6 | 96 | - | 114 |
| 8 | 4 | 6 | 6 | 96 | 10 | 118 |
| 9 | 2 | 6 | 6 | 60 | 17 | 89 |
| 14 | 5 | 12 | 6 | 84 | - | 102 |
| 16 | 5 | 12 | 6 | 216 | - | 234 |
| 15 | 11 | 18 | 6 | 132 | 22 | 178 |
| 17 | 9 | 6 | 6 | 288 | 10 | 310 |
| 18 | 8 | 6 | 6 | 96 | 10 | 118 |
| | | | | | Max. | 310 |
| | | | | | Min. | 89 |

CERAMIC EMITTER SUBSTRATE

CROSS-REFERENCE TO RELATED APPLICATIONS

The present application claims priority benefit under 35 U.S.C. §119(e) to U.S. Provisional Patent Application Ser. No. 60/998,659, filed Oct. 12, 2007, titled Ceramic Emitter Substrate; and U.S. Provisional Patent Application Ser. No. 61/192,131 filed Sep. 14, 2008, titled Ceramic Emitter Substrate; all of the above applications incorporated by reference herein.

INCORPORATION BY REFERENCE OF COPENDING RELATED CASES

The present disclosure is generally related to U.S. patent application Ser. No. 12/056,179, filed Mar. 26, 2008, titled Multiple Wavelength Optical Sensor, hereby incorporated by reference herein.

BACKGROUND OF THE INVENTION

Pulse oximetry systems for measuring constituents of circulating blood have gained rapid acceptance in a wide variety of medical applications, including surgical wards, intensive care and neonatal units, general wards, home care, physical training, and virtually all types of monitoring scenarios. A pulse oximetry system generally includes an optical sensor applied to a patient, a monitor for processing sensor signals and displaying results and a patient cable electrically interconnecting the sensor and the monitor. A pulse oximetry sensor has light emitting diodes (LEDs), typically one emitting a red wavelength and one emitting an infrared (IR) wavelength, and a photodiode detector. The emitters and detector are attached to a patient tissue site, such as a finger. The patient cable transmits drive signals to these emitters from the monitor, and the emitters respond to the drive signals to transmit light into the tissue site. The detector generates a signal responsive to the emitted light after attenuation by pulsatile blood flow within the tissue site. The patient cable transmits the detector signal to the monitor, which processes the signal to provide a numerical readout of physiological parameters such as oxygen saturation ($SpO_2$) and pulse rate. Advanced physiological monitoring systems utilize multiple wavelength sensors and multiple parameter monitors to provide enhanced measurement capabilities including, for example, the measurement of carboxyhemoglobin (HbCO), methemoglobin (HbMet) and total hemoglobin (Hbt).

Pulse oximeters capable of reading through motion induced noise are disclosed in at least U.S. Pat. Nos. 6,770,028, 6,658,276, 6,650,917, 6,157,850, 6,002,952, 5,769,785, and 5,758,644; low noise pulse oximetry sensors are disclosed in at least U.S. Pat. Nos. 6,088,607 and 5,782,757; all of which are assigned to Masimo Corporation, Irvine, Calif. ("Masimo") and are incorporated by reference herein.

Physiological monitors and corresponding multiple wavelength optical sensors are described in at least U.S. patent application Ser. No. 11/367,013, filed Mar. 1, 2006 and entitled Multiple Wavelength Sensor Emitters and U.S. patent application Ser. No. 11/366,208, filed Mar. 1, 2006 and entitled Noninvasive Multi-Parameter Patient Monitor, both assigned to Masimo Laboratories, Irvine, Calif. (Masimo Labs) and both incorporated by reference herein.

Further, physiological monitoring systems that include low noise optical sensors and pulse oximetry monitors, such as any of LNOP® adhesive or reusable sensors, SofTouch™ sensors, Hi-Fi Trauma™ or Blue™ sensors; and any of Radical®, SatShare™, Rad-9™, Rad-5™, Rad-5v™ or PPO+™ Masimo SET® pulse oximeters, are all available from Masimo. Physiological monitoring systems including multiple wavelength sensors and corresponding noninvasive blood parameter monitors, such as Rainbow™ adhesive and reusable sensors and RAD-57™ and Radical-7™ monitors for measuring $SpO_2$, pulse rate, perfusion index, signal quality, HbCO and HbMet among other parameters are also available from Masimo.

SUMMARY OF THE INVENTION

FIGS. 1A-B illustrate a physiological monitoring system 100 capable of generating $SpO_2$ and in multiple wavelength configurations additional blood parameter measurements such as HbCO, HbMet and Hbt. The physiological monitoring system 100 has a monitor 110 and a sensor 150. The sensor 150 attaches to a tissue site 1 and includes a plurality of emitters 122 capable of irradiating the tissue site with differing wavelengths of light, such as the red and infrared (IR) wavelengths utilized in pulse oximeters and, in some configurations, multiple wavelengths different than or in addition to those red and IR wavelengths. The sensor 150 also includes one or more detectors 154 capable of detecting the light after attenuation by the tissue site 1.

As shown in FIGS. 1A-B, the monitor 110 communicates with the sensor 150 to receive one or more intensity signals indicative of one or more physiological parameters and displays the parameter values. Drivers 114 convert digital control signals into analog drive signals capable of driving sensor emitters 152. A front-end 112 converts composite analog intensity signal(s) from light sensitive detector(s) 154 into digital data 115 input to the DSP 120. The digital data 115 is representative of a change in the absorption of particular wavelengths of light as a function of the changes in body tissue resulting from pulsing blood. The DSP 120 may comprise a wide variety of data and/or signal processors capable of executing programs for determining physiological parameters from input data.

Also shown in FIGS. 1A-B, the instrument manager 130 may comprise one or more microcontrollers controlling system management, such as monitoring the activity of the DSP 120. The instrument manager 130 also has a display driver 132, an audio driver 134 and an input/output (I/O) port 138 that provides a user and/or device interface for communicating with the monitor 110.

Further shown in FIGS. 1A-B are one or more user I/O devices 140 including a display 142, an audible indicator 144 and a keypad 148. The display 142 is capable of displaying indicia representative of calculated physiological parameters such as one or more of a pulse rate (PR), signal quality and values of blood constituents in body tissue, including for example, oxygen saturation ($SpO_2$). The monitor 110 may also be capable of storing or displaying historical or trending data related to one or more of the measured parameters or combinations of the measured parameters. Displays 142 include for example readouts, colored lights or graphics generated by LEDs, LCDs or CRTs to name a few. Audible indicators 144 include, for example, tones, beeps or alarms generated by speakers or other audio transducers to name a few. The user input device 148 may include, for example, a keypad, touch screen, pointing device, voice recognition device, or the like.

FIG. 2 illustrates an emitter array 200 for a multiple wavelength optical sensor having multiple emitters 210 capable of emitting light 202 having multiple wavelengths into a tissue site 1. Row drivers 270 and column drivers 280 are electrically connected to the emitters 210 and activate one or more emitters 210 by addressing at least one row 220 and at least one column 240 of an electrical grid. In one embodiment, the emitters 210 each include a first contact 212 and a second contact 214. The first contact 212 of a first subset 230 of emitters is in communication with a first conductor 220 of the electrical grid. The second contact 214 of a second subset 250 of emitters is in communication with a second conductor 240. Each subset comprises at least two emitters, and at least one of the emitters of the first and second subsets 230, 250 are not in common. A detector 290 is capable of detecting the emitted light 202 and outputting a sensor signal 295 responsive to the emitted light 202 after attenuation by the tissue site 1. As such, the sensor signal 295 is indicative of at least one physiological parameter corresponding to the tissue site 1, as described above.

FIG. 3 illustrates an emitter array 300 embodiment having light emitting diodes (LEDs) 301 connected within an electrical grid of n rows and m columns totaling n+m drive lines 350, 360, where n and m are integers greater than one. The electrical grid minimizes the number of drive lines required to activate the LEDs 301 while preserving flexibility to selectively activate individual LEDs 301 in any sequence and multiple LEDs 301 simultaneously. The electrical grid also facilitates setting LED currents so as to control intensity at each wavelength, determining operating wavelengths and monitoring total grid current so as to limit power dissipation. The emitter array 300 is also physically configured in rows 310. This physical organization facilitates clustering LEDs 301 according to wavelength so as to minimize pathlength variations and facilitates equalization of LED intensities.

As shown in FIG. 3, one embodiment of an emitter array 300 comprises up to sixteen LEDs 301 configured in an electrical grid of four rows 310 and four columns 320. Each of the four row drive lines 350 provide a common anode connection to four LEDs 301, and each of the four column drive lines 360 provide a common cathode connection to four LEDs 301. Thus, the sixteen LEDs 301 are driven with only eight wires, including four anode drive lines 312 and four cathode drive lines 322. This compares favorably to conventional common anode or cathode LED configurations, which require more drive lines.

Also shown in FIG. 3, row drivers 370 and column drivers 380 located in the monitor 110 selectively activate the LEDs 301. In particular, row and column drivers 370, 380 function together as switches to Vcc and current sinks to ground, respectively, to activate LEDs and as switches to ground and Vcc, respectively, to deactivate LEDs. This push-pull drive configuration prevents parasitic current flow in deactivated LEDs. In a particular embodiment, only one row drive line 350 is switched to Vcc at a time. One to four column drive lines 360, however, can be simultaneously switched to a current sink so as to simultaneously activate multiple LEDs within a particular row. Activation of two or more LEDs of the same wavelength facilitates intensity equalization.

A ceramic emitter substrate advantageously houses, mechanically mounts and electrically interconnects an emitter array, as described with respect to FIGS. 2-3, above. Ceramic lends mechanical and structural precision over other substrate materials. Further, the ceramic substrate provides uniform thermal properties that allow accurate measurement of emitter temperatures utilizing a co-mounted thermistor or similar temperature responsive device. The ceramic substrate also provides a cavity which protects the emitter array and accepts encapsulants. Encapsulants may include one or more of an attenuating epoxy over selected emitter components so as to equalize emitter intensities and clear fill epoxy with or without a dispersed diffusing media, as examples. In addition, the ceramic media is multi-layered, allowing internal routing for the matrix that interconnects the emitter array. A ceramic emitter substrate incorporated into an optical sensor and also encapsulants disposed in a ceramic emitter substrate cavity are described with respect to U.S. patent application Ser. No. 12/056,179, cited above and incorporated by reference herein.

In particularly advantageous embodiments, special attention is given to the ceramic substrate multi-layer conductors to achieve very low resistance. Low resistance in the emitter array interconnect minimizes the resistive heating of the substrate and corresponding spurious wavelength shifts. Also, low interconnect resistance lessens parasitic voltage drops between emitters and drivers that negatively impact available drive current.

One aspect of a ceramic emitter substrate is an optical medical device that transmits optical radiation into a fleshy tissue site. The optical radiation is detected after absorption by pulsatile blood flow within the fleshy tissue site so as to compute constituents of the pulsatile blood flow. A generally rectangular-cross-sectioned ceramic body has a top side, a bottom side and an edge adjoining the sides. A cavity is defined by the ceramic body and disposed on the top side. Conductive bonding pads are disposed within the cavity. Conductive solder pads are disposed on the bottom side proximate the edge. Conductive traces and vias form an interconnect of the bonding pads and the solder pads. Light emitting diodes (LEDs) can be attached to the bonding pads and individually activated as an emitter array via row and column drive signals applied to the solder pads in order to transmit optical radiation out of the cavity.

In an embodiment, the ceramic body comprises first, second, third and fourth layers. The first layer defines the top side and the cavity. The second layer underlies the first layer. The third layer underlies the second layer. A fourth layer underlies the third layer and defines the bottom side. A first portion of the bonding pads are disposed on the second layer. A second portion of the bonding pads are disposed on the third layer. LEDs are mounted to the bonding pads on the third layer and wire bonded to the bonding pads on the second layer. In a particularly advantageous embodiment, each combination of traces, vias and pads constituting a conductive path between the solder pads and the bonding pads for any one of the drive signals has a combined resistance less than about 310 milliohms.

In an embodiment, a thermistor is mounted within the cavity and electrically connected to the bonding pads so that the resistance of the thermistor can be read via the solder pads and the interconnect. A portion of the third layer creates a raised partition within the cavity that separates the floor of the cavity into a first area and a second area. LEDs are mounted within the first area and the thermistor is mounted within the second area. An encapsulant may be disposed within the cavity over at least a portion of the LEDs, where the encapsulant functions as an optical filter or an optical diffuser or both. In a particularly advantageous embodiment, the ceramic body is constructed of a substantially light absorbing material so as to substantially block LED emitted optical radiation from being transmitted through the ceramic body.

Another aspect of a ceramic emitter substrate comprises a ceramic body having a top side, an opposite bottom side and an edge disposed between and along the periphery of the top and bottom sides. The ceramic body has a first layer corresponding to the top side, a second layer adjacent the first layer, a third layer adjacent the second layer and a fourth layer corresponding to the bottom side. A cavity is defined by the first layer. Solder pads are disposed on the fourth layer on the bottom side proximate the edge. Bonding pads are disposed on the second layer and on the third layer. The bonding pads are accessible via the cavity. Traces are disposed on the second, third and fourth layers and vias are disposed between the second, third and fourth layers so as to interconnect the solder pads and the bonding pads.

In a particularly advantageous embodiment, the traces have a substantial width relative to the area of the ceramic body sides so as to have a low resistance. In an embodiment, the resistance of any one of the traces is less than about 290 milliohms. In an embodiment, the ceramic body measures about 0.23×0.15×0.04 inches and the cavity measures about 0.18×0.10 inches. In an embodiment, the ceramic body comprises a dark material that substantially absorbs light transmitted from the light emitting diodes so as to substantially block optical leakage through the ceramic body edge and bottom side.

A further aspect of a ceramic emitter substrate is a method of constructing an optical sensor having emitters that transmit optical radiation having multiple wavelengths into a tissue site and a detector that generates a sensor signal responsive to the optical radiation after absorption by the tissue site. A ceramic substrate having a top side and a bottom side is provided. A cavity is defined in the top side of the ceramic substrate. Light emitting devices are mounted within the cavity. Low-resistance conductors are routed on and within the ceramic substrate so as to transmit drive signals to the light emitting devices from a source external to the ceramic substrate.

In various embodiments bonding pads are plated on the top side within the cavity. Solder pads are plated on the bottom side. The solder pads are interconnected with the bonding pads. The light emitting devices are bonded to the bonding pads so as to transmit optical radiation from the cavity in response to drive signals applied to the solder pads. In an embodiment, plating bonding pads comprises plating upper bonding pads on a second layer of the ceramic substrate, plating lower bonding pads on a third layer of the ceramic substrate and sandwiching the second layer and the third layer between a first layer of the ceramic substrate that defines the top side and the cavity and a fourth layer that defines the bottom side. In an embodiment, Interconnecting comprises disposing traces on the second, third and fourth layers, which may comprise substantially maximizing the width of each of the traces that conduct the drive signals given the number of traces and the area of the layers so as to substantially minimize the resistance of the traces. In an embodiment, traces of sufficient width are provided so that each of the traces that conduct the drive signals has a resistance less than about 290 milliohms. Solder pads, bonding pads and vias are provided so that the resistance from solder pad to bonding pad for each of the drive signals is less than about 310 milliohms.

Another aspect of a ceramic emitter substrate is configured to mount in an optical sensor and to transmit optical radiation into a fleshy tissue site, the optical radiation detected after absorption by pulsatile blood flow, a signal responsive to the detected optical radiation communicated to a monitor that computes constituents of the pulsatile blood flow. The ceramic emitter substrate comprises a ceramic substrate means for housing LEDs. A solder pad means is for physically mounting and electrically interconnecting the ceramic substrate means to a sensor. Bonding pad means are for mounting and electrically interconnecting the LEDs to the ceramic substrate means. Low resistance conductive means are for interconnecting the solder pad means and the bonding pad means.

In various embodiments, the ceramic substrate means comprises a first ceramic layer means for defining a cavity within the ceramic substrate means. A third ceramic layer means is for defining a device bonding area along a cavity floor. A second ceramic layer means is for defining a wire bonding area raised above the cavity floor disposed between the first and second ceramic layer means. A fourth ceramic layer means is for defining a soldering area disposed adjacent the third ceramic layer means. A first set of the bonding pad means is for mounting electrical components disposed along the device bonding area. A second set of the bonding pad means is for wiring bonding to electrical components disposed along the wire bonding area. Solder pad means are for soldering the ceramic substrate to a flexible circuit disposed along the soldering area. Low resistance conductive means are for interconnecting between the solder pad means and the first and second sets of bonding pad means.

BRIEF DESCRIPTION OF THE DRAWINGS

FIGS. 6-14 are views of a ceramic emitter substrate embodiment;

FIG. 7 is a plan view of ceramic emitter substrate bonding pads;

FIGS. 8-11 are plan views of ceramic emitter substrate first through fourth layers;

FIG. 12-13 are plan views of ceramic emitter substrate solder pads and an alumina coat layer, respectively;

FIGS. 15-23 are views of a low-resistance ceramic emitter substrate embodiment;

FIG. 15 is a resistance chart for a low-resistance ceramic emitter substrate;

FIG. 17 is a bonding plan view of a low-resistance ceramic emitter substrate;

FIGS. 18-21 are plan views of first through fourth layers, respectively, for a low-resistance ceramic emitter substrate embodiment; and FIGS. 22-23 are plan views of solder pads and an alumina coat layer, respectively, for a low-resistance ceramic emitter substrate.

DETAILED DESCRIPTION OF THE PREFERRED EMBODIMENTS

Figure 1A:
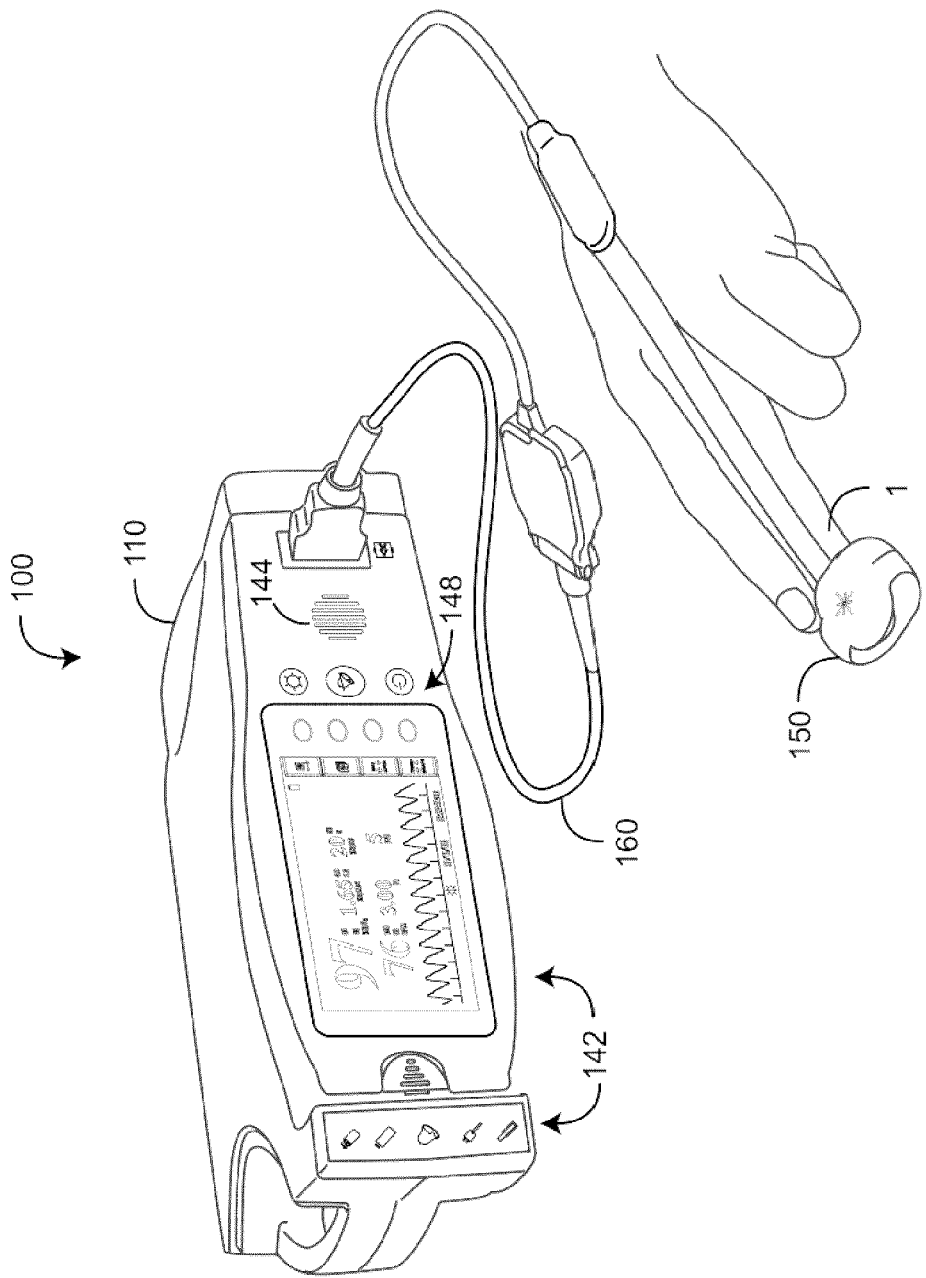
FIGS. 1A-B are a perspective view and general block diagram of a physiological measurement system utilizing an optical sensor.
Figure 1B:
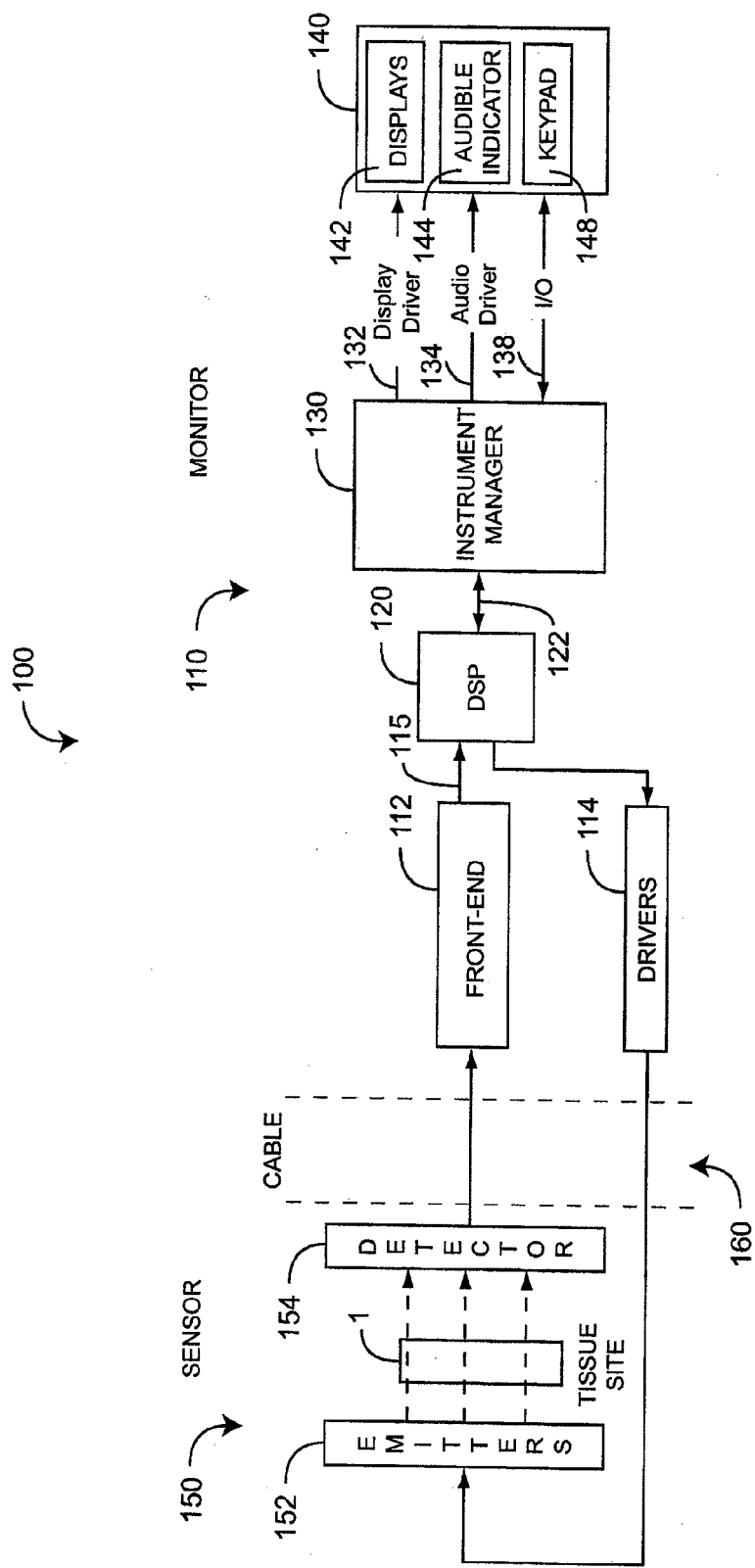
Figure 4B:
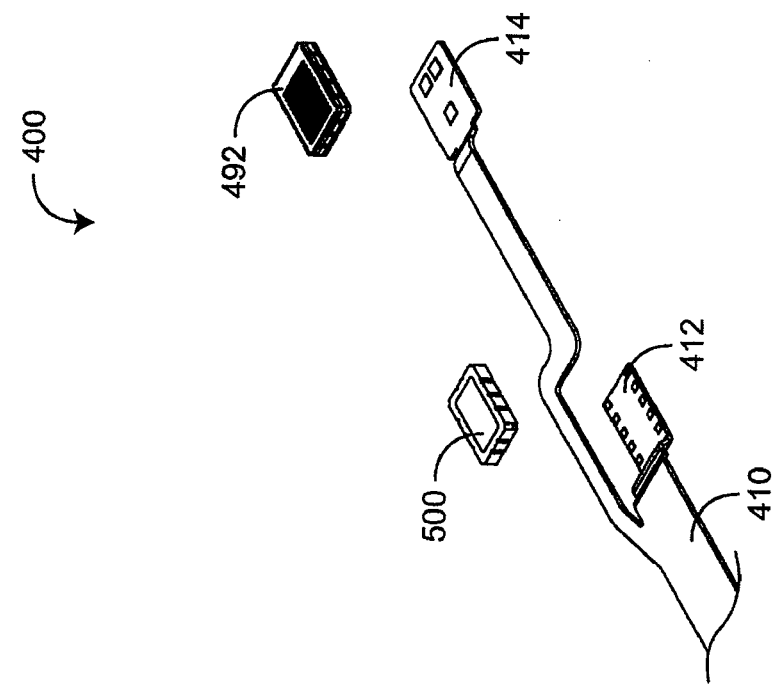
FIGS. 4A-B are top and bottom exploded views of a multiple wavelength sensor assembly utilizing a ceramic emitter substrate.
Figure 4A:
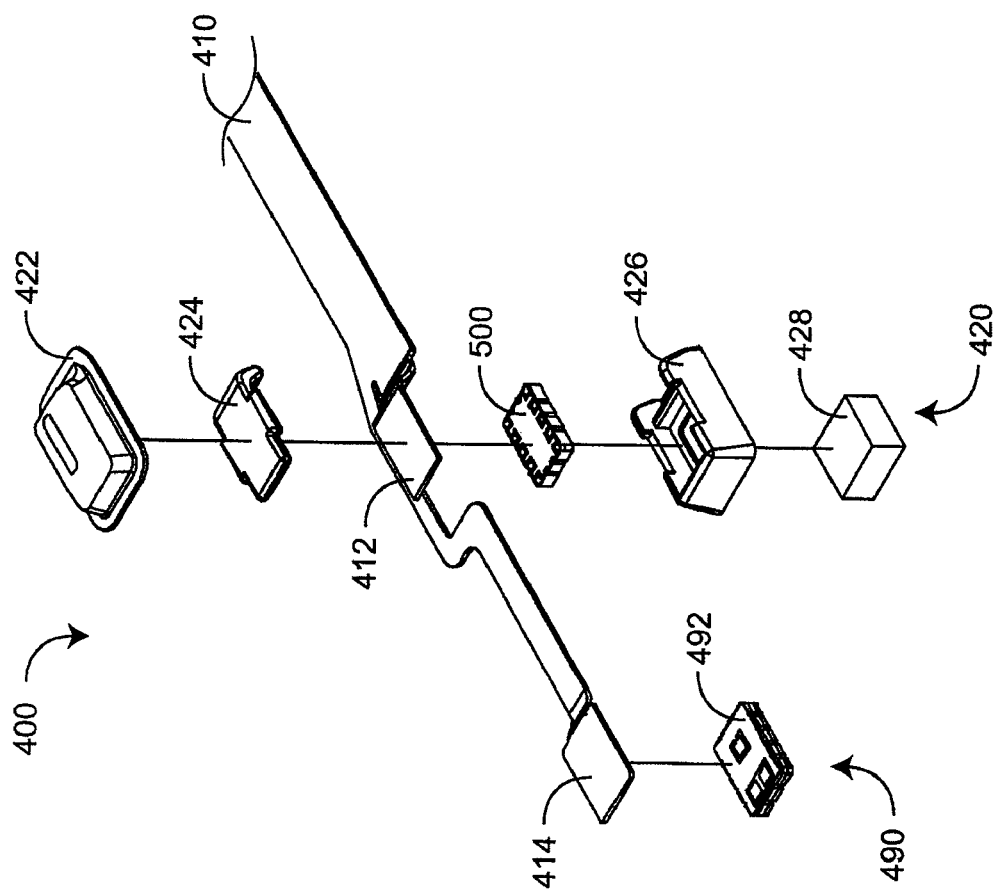
Figure 12:
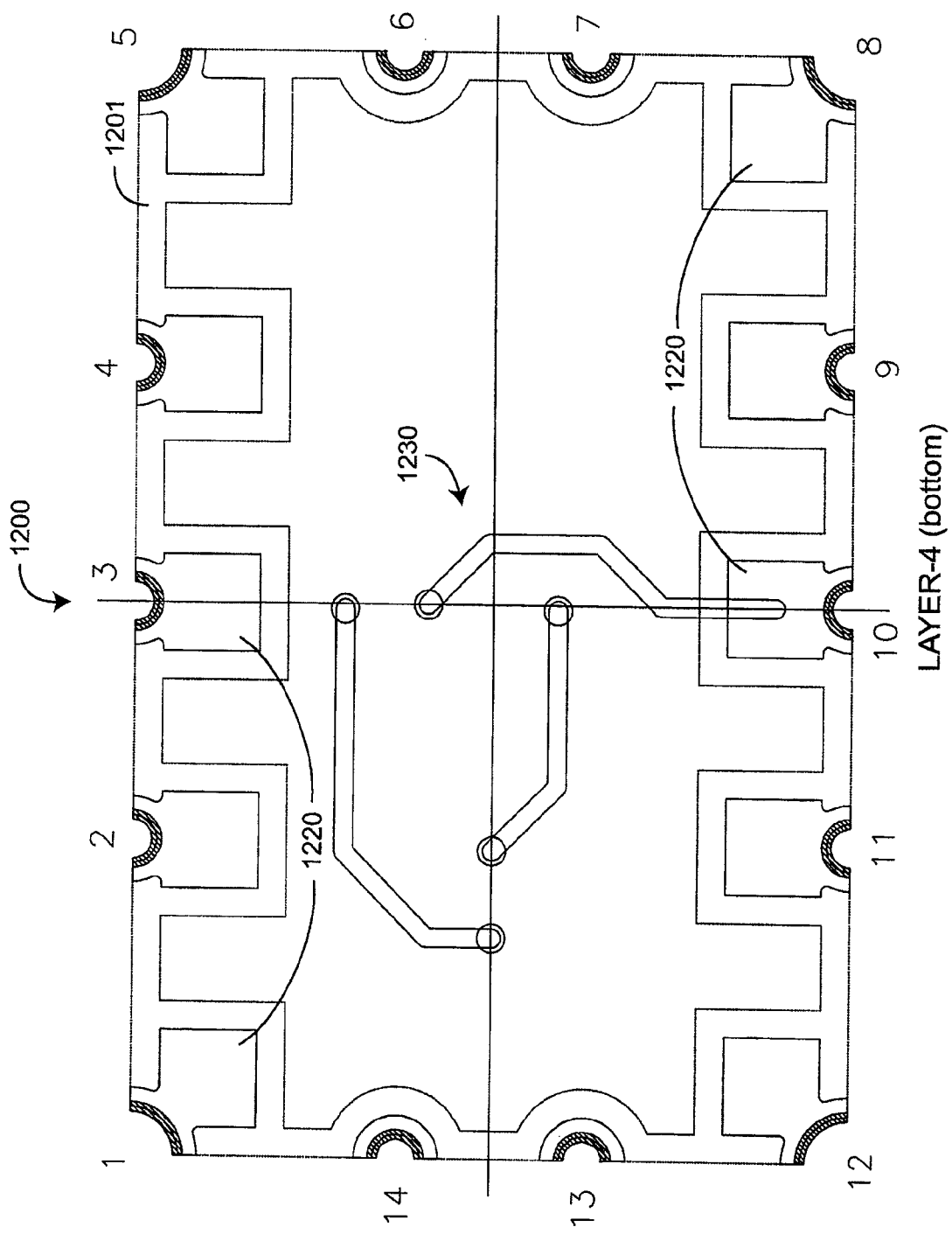

FIGS. 4A-B illustrate an interconnect assembly 400 having a flex circuit 410, an emitter assembly 420 and a detector assembly 490. The flex circuit 410 mounts the emitter assembly 420 and detector assembly 490, connects to a sensor cable 160 (FIGS. 1A-B) and provides electrical communications between a monitor 110 (FIGS. 1A-B) and emitters mounted in a ceramic emitter substrate 500. The emitter assembly 420 has a cover 422, a light block 424, a ceramic emitter substrate 500, a spacer 426 and an encapsulant 428. The ceramic emitter substrate 500 is soldered to an emitter mount 412 on the flex circuit 410. Similarly a ceramic-carrier detector 492 is soldered to a detector mount 414. In particular, the emitter mount solder pads correspond to ceramic substrate solder pads 1220 (FIG. 12).

Advantageously, the spacer 426 and encapsulant 428 provide a relatively uniform illumination of patient tissue across all emitted wavelengths. In particular, the spacer 426 provides a gap between an emitter array mounted in the ceramic substrate 500 and a tissue site, allowing the light from each emitter to spread as it propagates to the tissue site. Further, the encapsulant 428 can be configured to diffuse or scatter emitter light from each emitter as it propagates to a tissue site. In an embodiment, the encapsulant contains glass beads in a clear silicon RTV. In an embodiment, the encapsulant also contains a filtering medium that provides pass-band characteristics according to emitted wavelengths so as to equalize intensities of the various emitters. In an embodiment, the encapsulant provides notch filter characteristics according to emitted wavelengths so as to substantially attenuate secondary emissions from one or more emitters.

Figure 3:
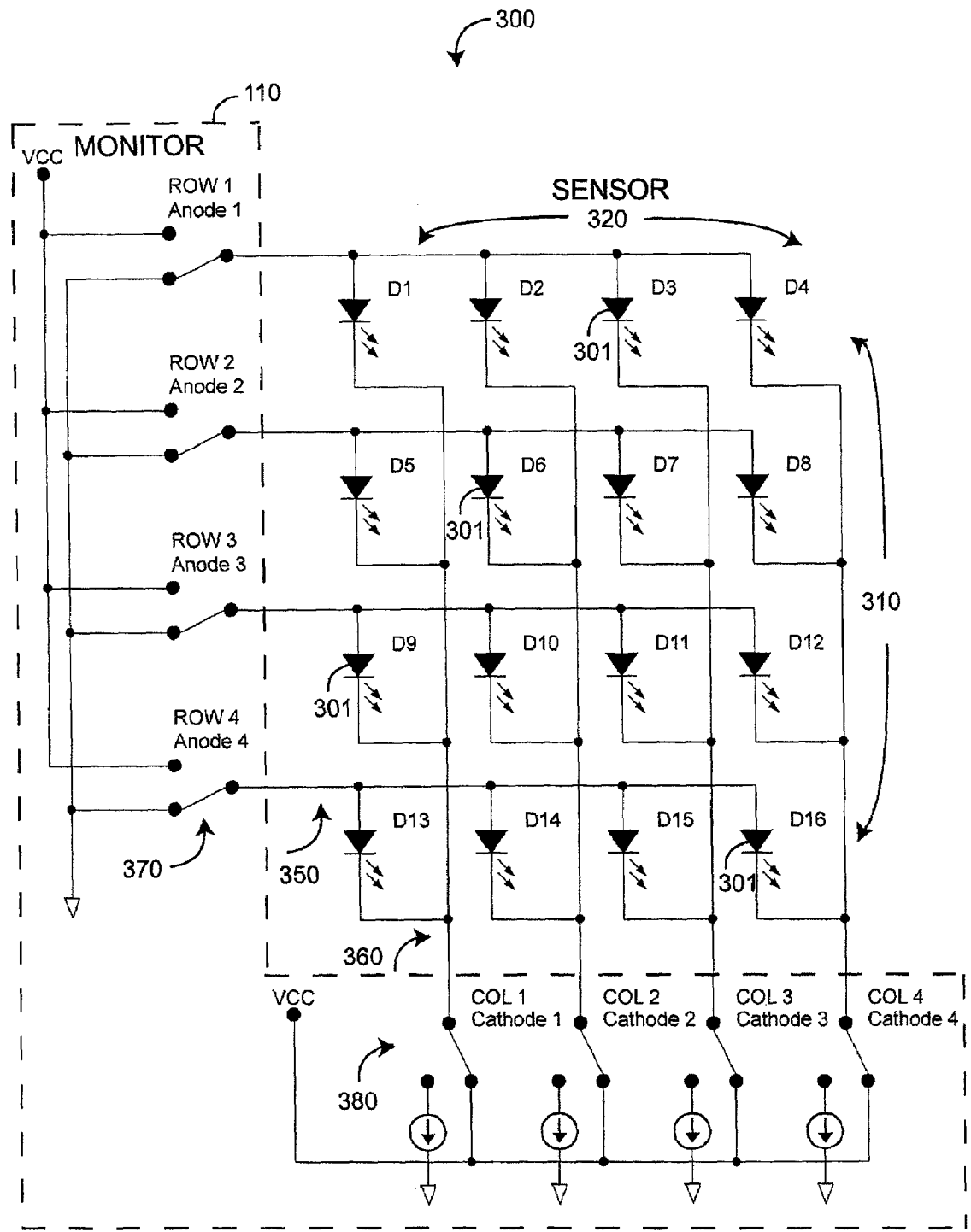
FIG. 3 is a schematic diagram of an emitter array.
Figure 5A:
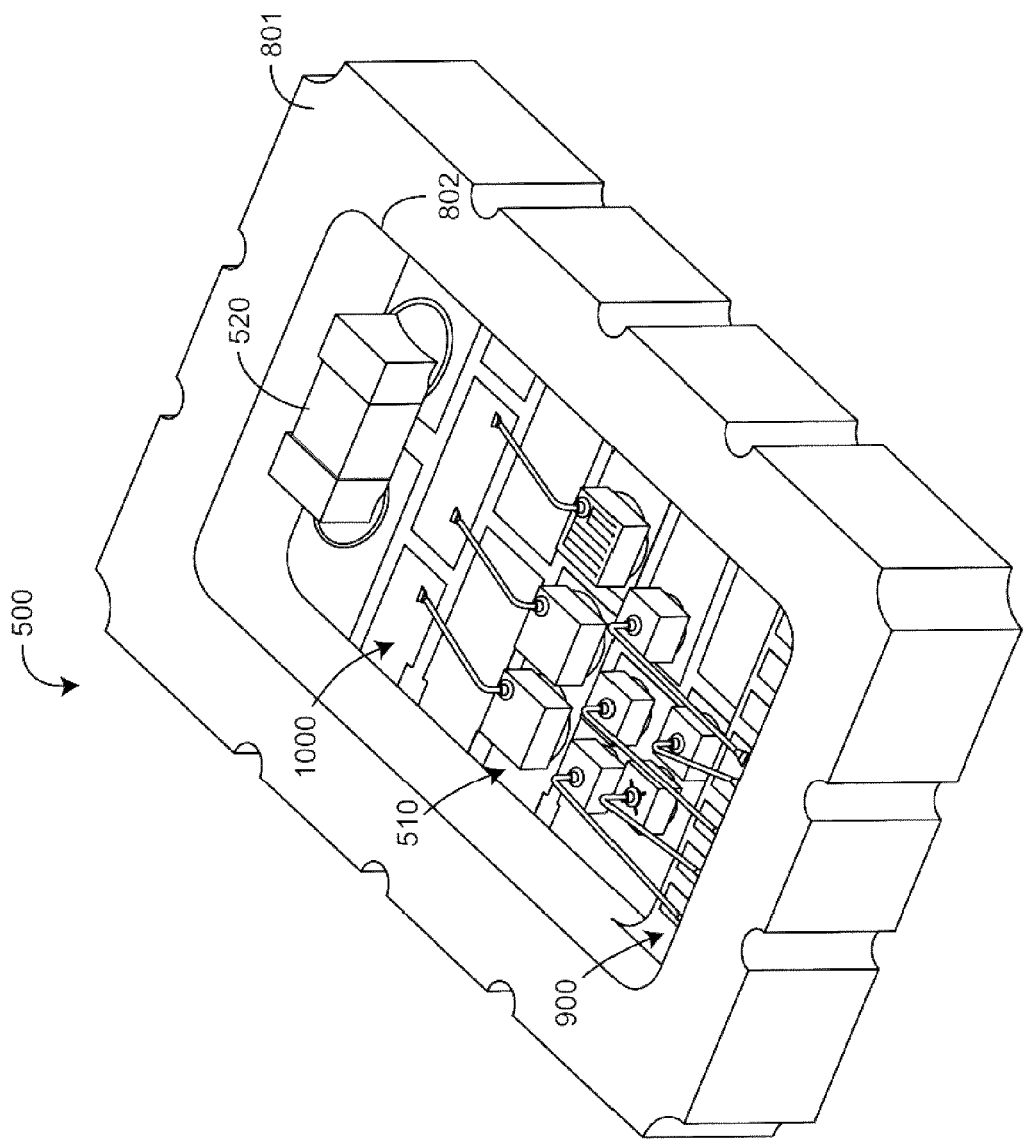
FIGS. 5A-B are perspective and perspective cross sectional views, respectively, of a ceramic emitter substrate.
Figure 5B:
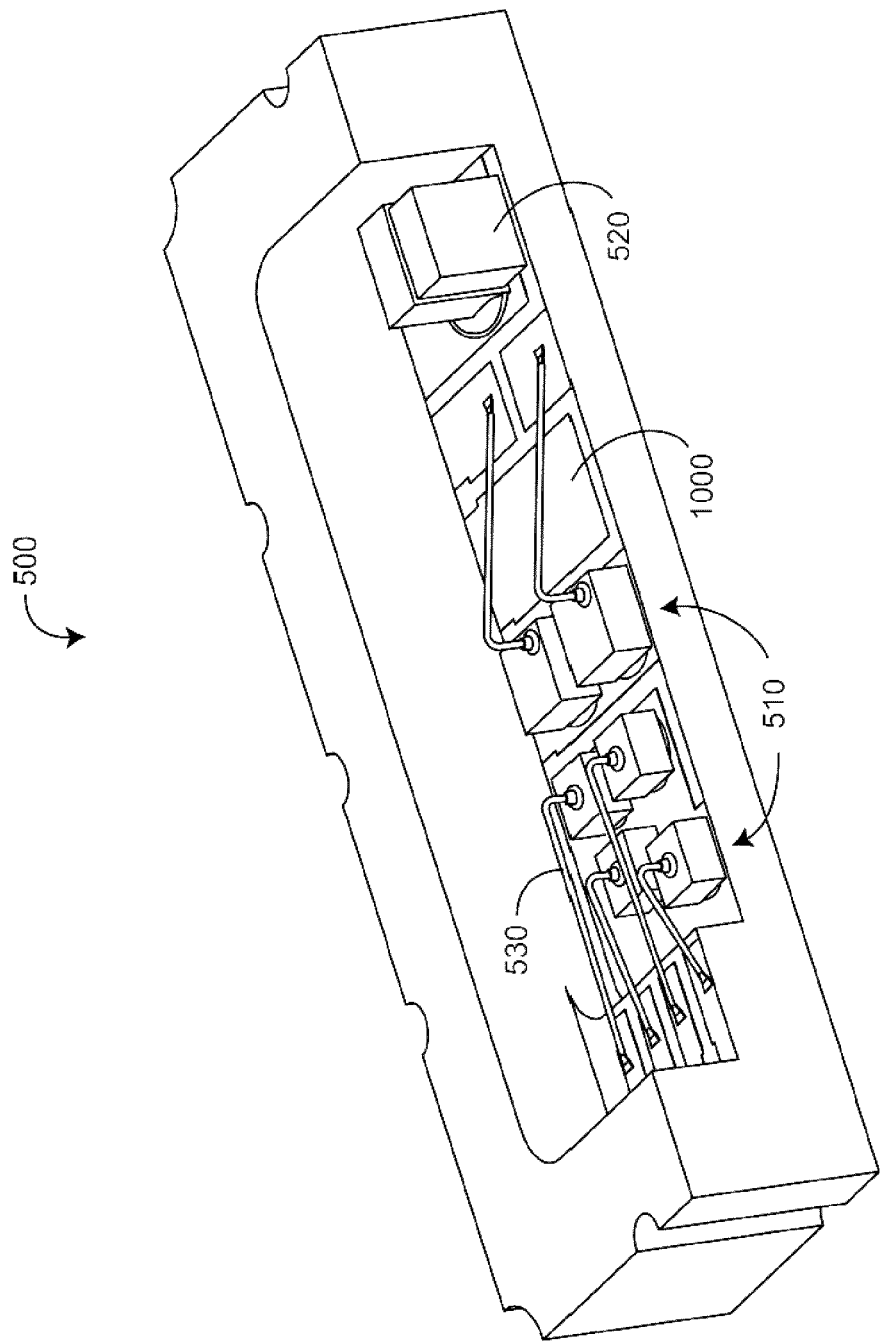

FIGS. 5A-B illustrate a ceramic emitter substrate 500 having multiple layers of bonding pads, traces, vias and solder pads so as to mount and interconnect an emitter array, e.g. 300 (FIG. 3). The ceramic emitter substrate 500 has a body 801 defining a cavity 802. The cavity 802 contains LEDs 510 connected to bonding pads 900, 1000. The cavity 802 also contains a thermistor 520, the resistance of which can be measured in order to determine the bulk temperature of the LEDs 510. The thermal characteristics of ceramic stabilize and normalize the bulk temperature of the substrate 500 so that the thermistor measurement of bulk temperature is meaningful.

FIGS. 6-14 illustrate an embodiment of a ceramic emitter substrate. In particular, FIGS. 6A-D illustrate a ceramic emitter substrate 500 having a top side 601 and a bottom side 602. The top side 601 has upper bonding pads 910 and lower bonding pads 1010 as described with respect to FIG. 7, below. The bottom side 602 has solder pads 1220, as described with respect to FIG. 12, below. The ceramic emitter substrate 500 also has four layers 800, 900, 1000, 1100 with corresponding surfaces including bonding pads, traces, vias and solder pads, as described with respect to FIGS. 8-11, below.

Figure 6C:
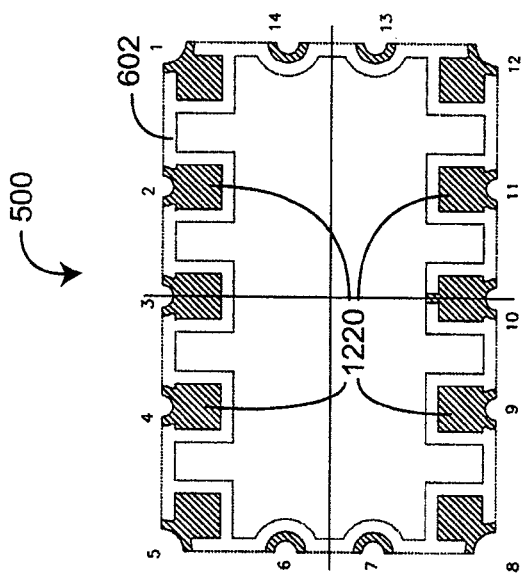
FIGS. 6A-D are top, half-end cross sectional, bottom and half-side cross sectional views, respectively, of a ceramic emitter substrate.
Figure 6B:
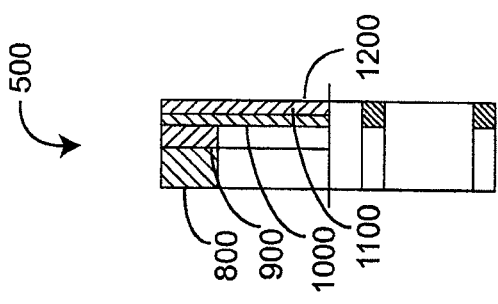
Figure 6A:
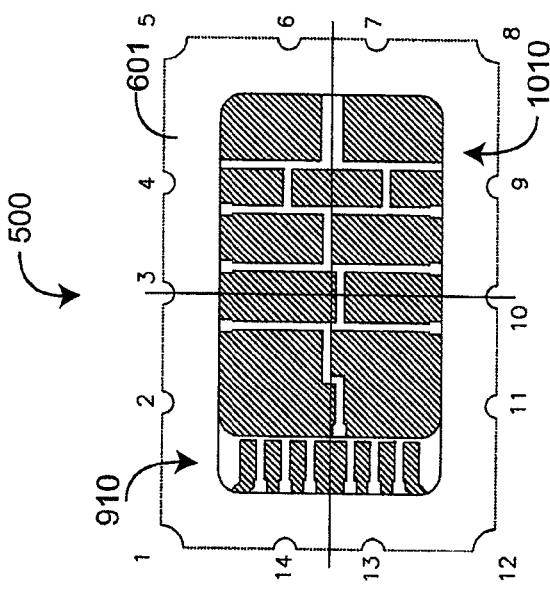
Figure 6D:
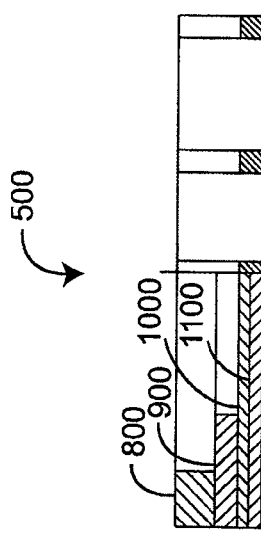
Figure 7:
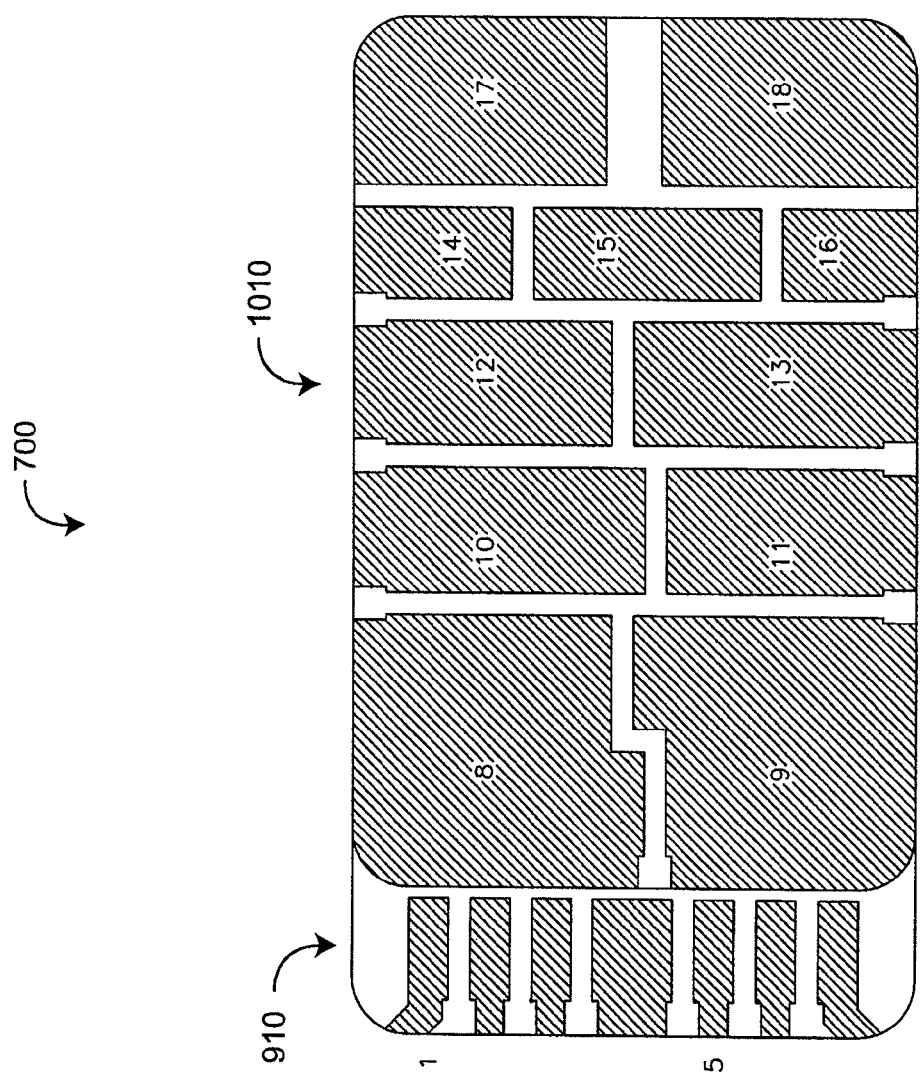

FIG. 7 illustrates upper 910 and lower 1010 bonding pads. The lower bonding pads 1010, labeled 8 through 16, mount and electrically connect a first side (anode or cathode) of the LEDs 510 (FIG. 5A) into an emitter array. Upper bonding pads 910, labeled 1 through 7, electrically connect a second side (cathode or anode) of the LEDs 510 (FIG. 5A) into the emitter array, via bonding wires 530 (FIG. 5B). A thermistor 520 is mounted to bonding pads 1010 labeled 17 and 18. Plated "feed-thru" holes and other vias electrically connect the bonding pads 910, 1010 on the top side 601 (FIG. 6A) with the solder pads 1220 (FIG. 6C) on the bottom side 602 (FIG. 6C). In one embodiment, top-side 601 (FIG. 6A) bonding pad numbers and corresponding bottom-side 602 (FIG. 6C) solder pad numbers are electrically connected as shown in TABLE 1.

TABLE 1

Connection Table

| BOND PAD NO. | SOLDER PAD NO. |
|---|---|
| 1 | 1 |
| 6 | |
| 11 | |
| 2 | 10 |
| 7 | |
| 12 | |
| 3 | 12 |
| 5 | |
| 13 | |
| 4 | 3 |
| 10 | |
| 8 | 2 |
| 9 | 11 |
| 14 | 5 |
| 16 | |
| 15 | 4 |
| 17 | 9 |
| 18 | 8 |
| | 6 |
| | 7 |
| | 13 |
| | 14 |

Figure 8:
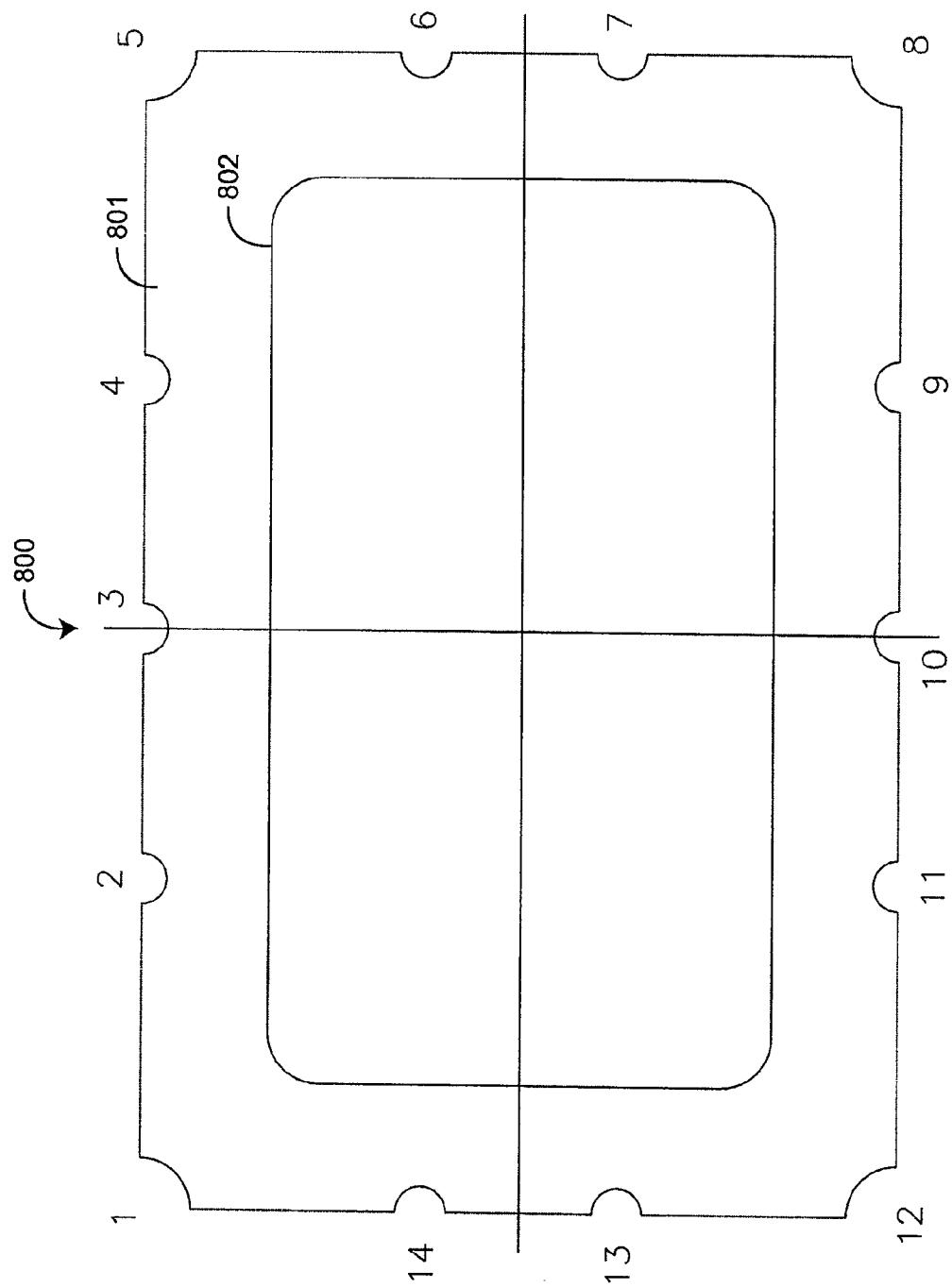

FIG. 8 illustrates a first layer 800 defining the ceramic substrate top side 601 (FIG. 6A). The first layer 800 has a generally rectangular ceramic body 801 defining a generally rectangular cavity 802.

Figure 9:
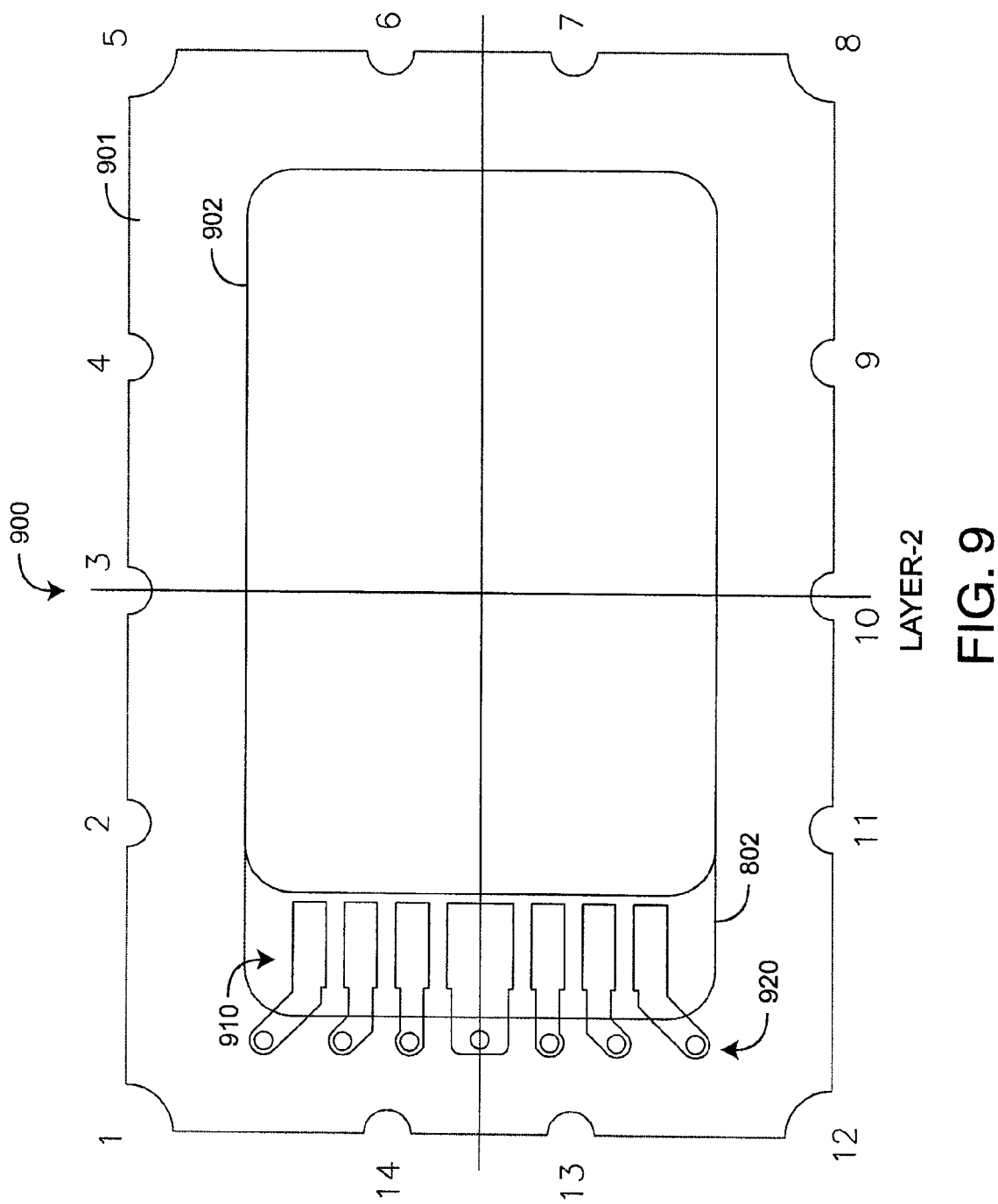

FIG. 9 illustrates a ceramic substrate second layer 900 proximate the first layer 800 (FIG. 8). The second layer 900 has a generally rectangular body 901 having an outer perimeter coextensive with that of the first layer 801 (FIG. 8). The body 901 defines a generally rectangular cavity 902 having a length less than that of the first layer cavity 801, so as to form a shelf for the upper bonding pads 910. The first layer body 801 extends over traces and vias 920 extending from the upper bonding pads 910.

Figure 10:
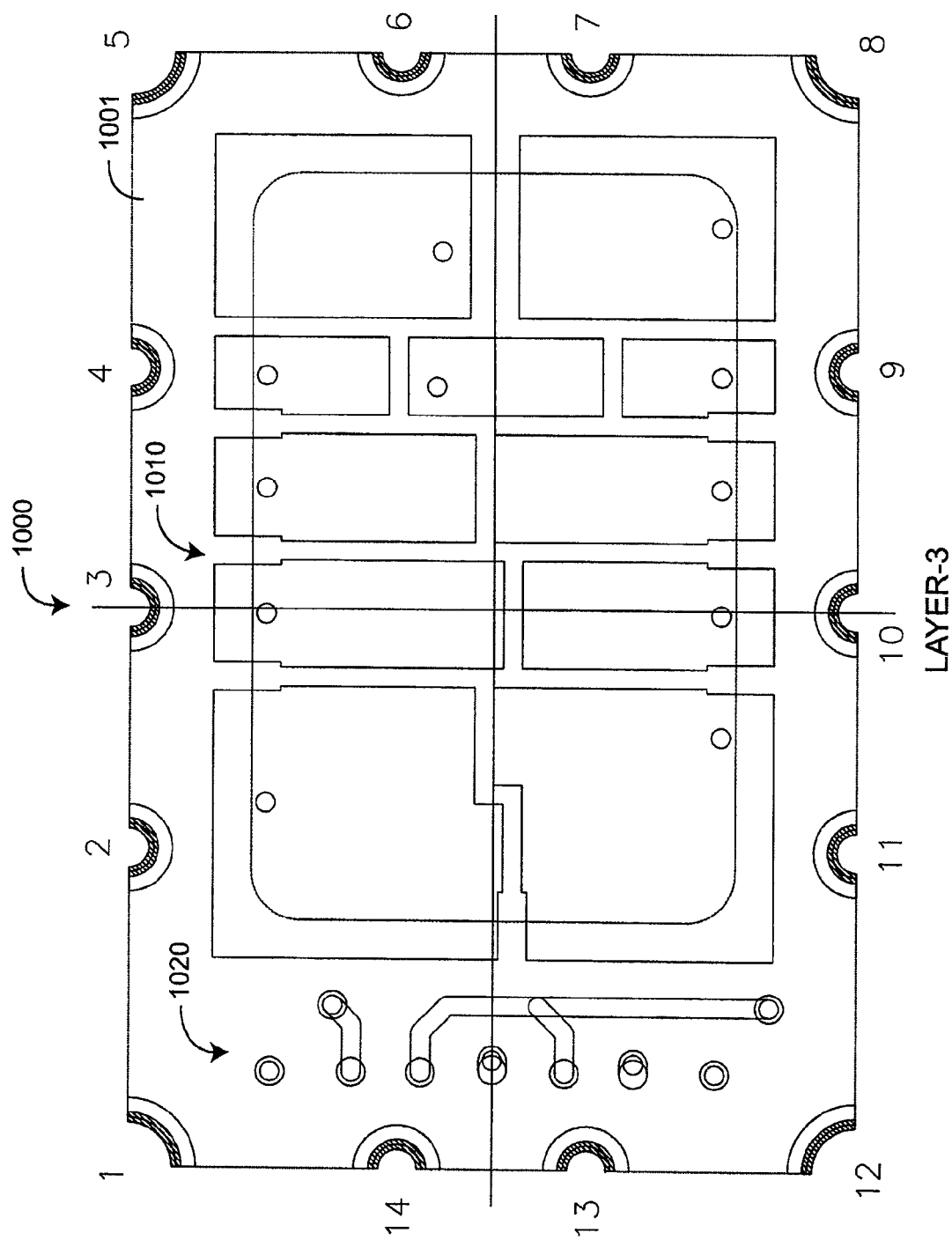

FIG. 10 illustrates a ceramic substrate third layer 1000 proximate the second layer 900 (FIG. 9). The third layer 1000 has a generally rectangular body 1001 having an outer perimeter coextensive with that of the first layer 801 (FIG. 8) and second layer 901 (FIG. 9). Lower bonding pads 1010 are disposed on a top surface of the third layer 1000 proximate the ceramic substrate top side 601 (FIG. 6A) and distal the ceramic substrate bottom side 602 (FIG. 6C). The bonding pads 1010 are at least substantially exposed through the first and second layer cavities 802, 902 (FIGS. 8-9). Traces and vias 1020 are also disposed on a top surface of the third layer 1000 so as to be covered by the second layer body 901.

Figure 11:
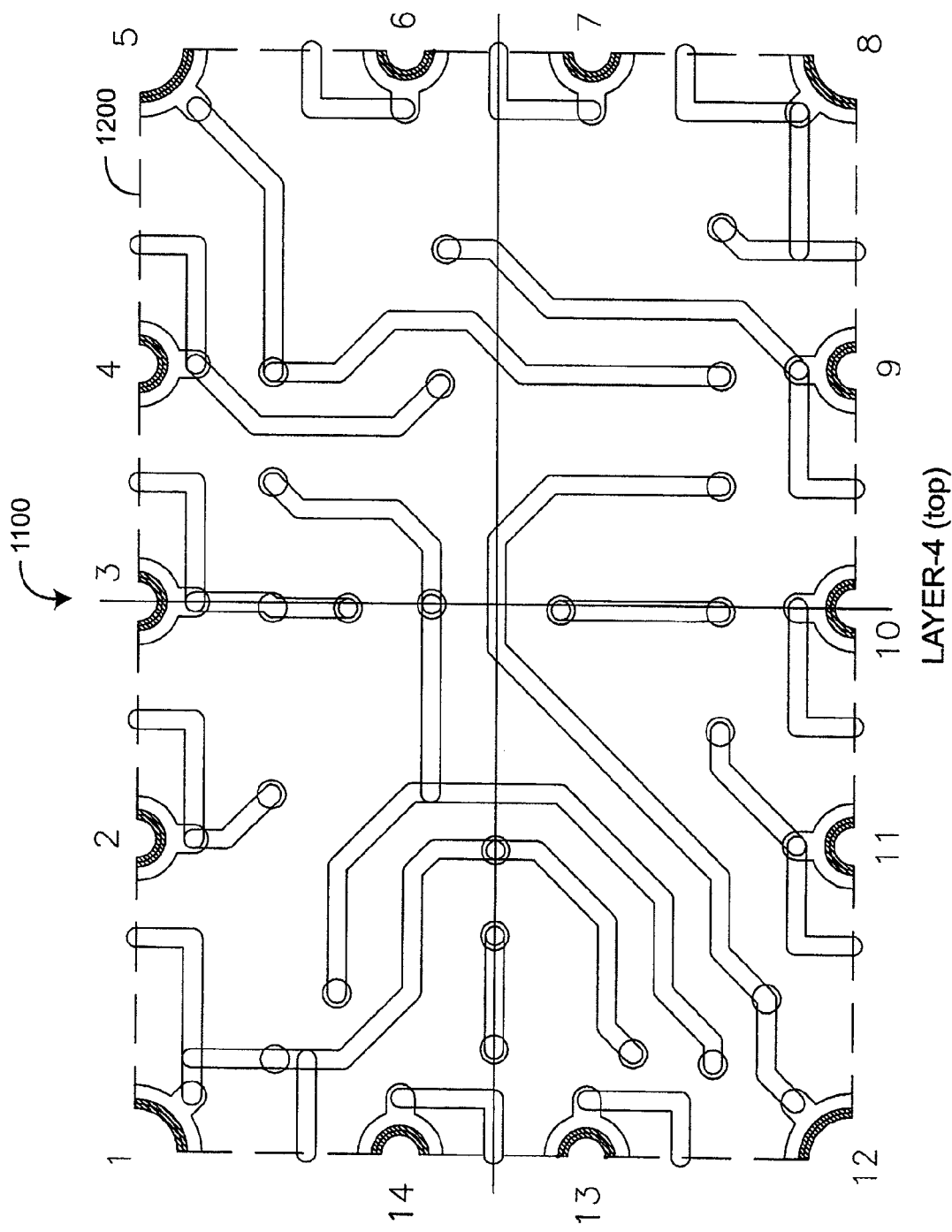

FIG. 11 illustrates traces and vias 1100 disposed on a top side of a fourth layer 1200 proximate the ceramic substrate top side 601 (FIG. 6A) and distal the ceramic substrate bottom side 602 (FIG. 6C). The traces and vias 1100 are wholly covered by the third layer body 1001.

FIG. 12 illustrates a ceramic substrate fourth layer 1200 proximate the third layer 1000 (FIG. 10). The fourth layer 1200 has a generally rectangular body 1201 having an outer perimeter coextensive with that of the first through third layers 801, 901, 1001 (FIGS. 8-10). Solder pads 1220 and traces and vias 1230 are disposed on a bottom side of the fourth layer 1200, which is the ceramic substrate bottom side 602 (FIG. 6C). In an embodiment, an alumina coat 1300 (FIG. 13) extends over at least a substantial portion of the bottom side 602 (FIG. 6C) so as to coat the traces and vias 1230 and leave exposed the solder pads 1220.

Figures 14A, 14B, 14C:
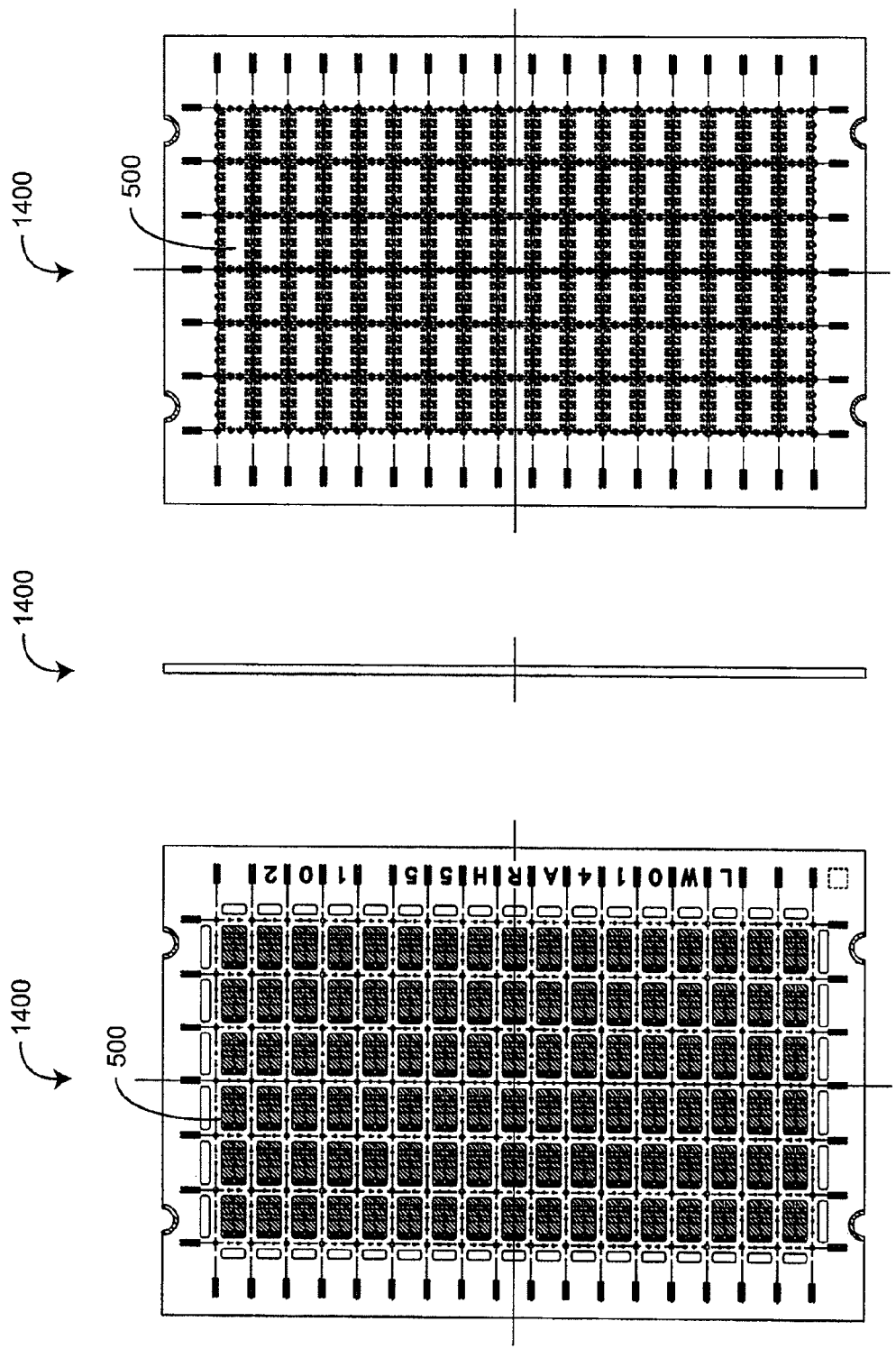
FIGS. 14A-C are top, side and bottom views of an array of ceramic emitter substrates formed from a multilayer ceramic sheet.

FIGS. 14A-C illustrate top, side and bottom views of a multilayer ceramic sheet 1400 manufactured with a 6×17 matrix of ceramic emitter substrates. The multilayer ceramic sheet 1400 is sliced during manufacture so as to separate and provide 102 individual ceramic emitter substrates 500, as described above.

FIGS. 15-23 illustrate a low-resistance embodiment of a ceramic emitter substrate. Advantageously, a low-resistance ceramic emitter substrate provides multi-layer conductors (including traces, pads, contacts and vias) that are configured with respect to one or more design goals of maximizing conductor cross-sectional area (trace width×trace thickness) and minimizing trace length within the physical constraints of the ceramic substrate so as to achieve very low resistance in the interconnect between emitter drivers and the emitters. In an embodiment, contact resistance is also minimized by selection of high conductivity conductor materials. Low resistance in the emitter array interconnect minimizes the resistive heating of the substrate and corresponding spurious emitter wavelength shifts. Also, low interconnect resistance lessens parasitic voltage drops between drivers and emitters that negatively impact available drive current and, hence, emitter intensity.

Figure 2:
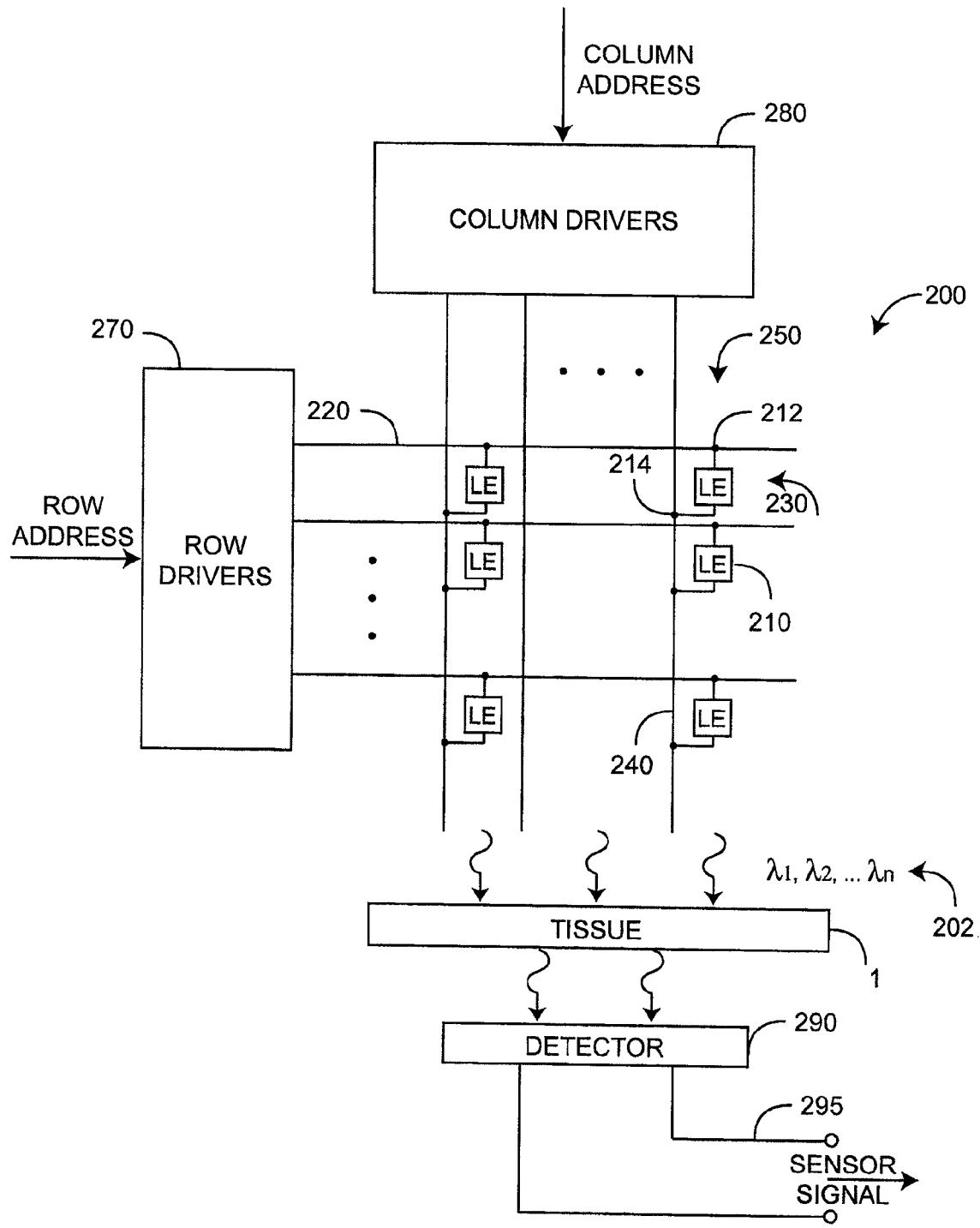
FIG. 2 is a general block diagram of an emitter array for a multiple wavelength optical sensor.

FIG. 15 is a conductor resistance chart for an embodiment of a low-resistance ceramic emitter substrate. Conductor design goals for this embodiment focused on maximizing conductor width and minimizing length. Conductors are a 30 µinch gold plate over 100 µinch nickel on an underlying tungsten/copper ink. In a particularly advantageous embodiment, each combination of traces, vias and pads constituting a conductive path between the ceramic emitter substrate solder pads and bonding pads for any one of the LED drive signals, described with respect to FIGS. 2-3 above, has a combined resistance less than about 310 milliohms. Traces of sufficient width are provided so that each of the traces that conduct the drive signals has a resistance less than about 290 milliohms.

FIGS. 16A-D illustrate a ceramic emitter substrate 1600 having a top side 1601, a bottom side 1602 and an edge 1603. A cavity 1604 extends from the top side 1601 into the substrate body to a cavity floor 1605. The top side 1601 has upper bonding pads 1910 and lower bonding pads 2010 as described with respect to FIG. 17, below. The bottom side 1602 has solder pads 2220, as described with respect to FIG. 22, below. The ceramic emitter substrate 1600 also has four layers 1800, 1900, 2000, 2100 with corresponding surfaces including bonding pads, traces, vias and solder pads, as described with respect to FIGS. 18-21, below. In an embodiment, the ceramic body measures about 0.23×0.15×0.04 inches and the cavity measures about 0.18×0.10 inches.

Figure 16C:
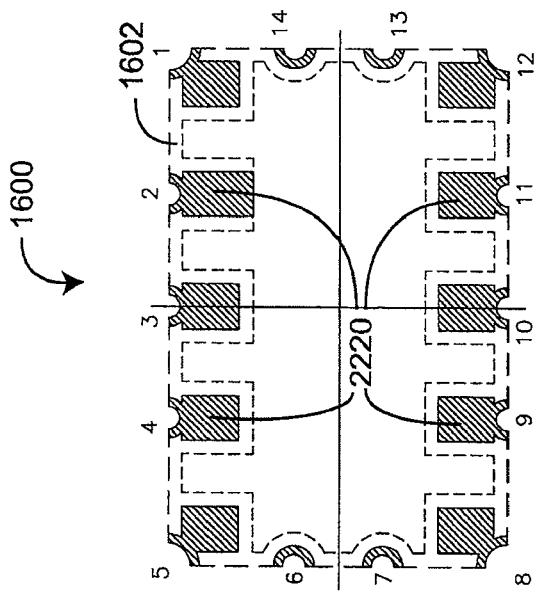
FIGS. 16A-F are top, half-end cross sectional, bottom and half-side cross sectional views and top and bottom perspective views, respectively, of a low-resistance ceramic emitter substrate.
Figure 16B:
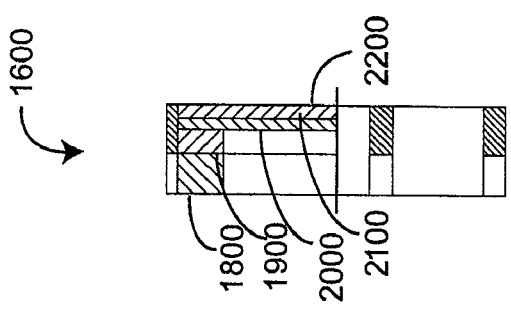
Figure 16A:
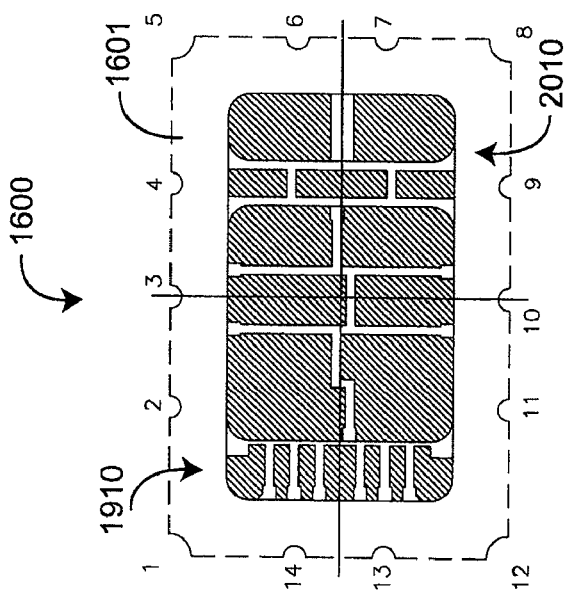
Figure 16D:
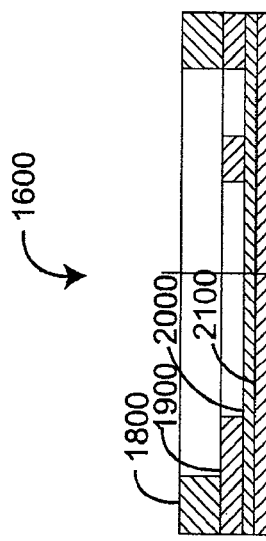
Figure 16F:
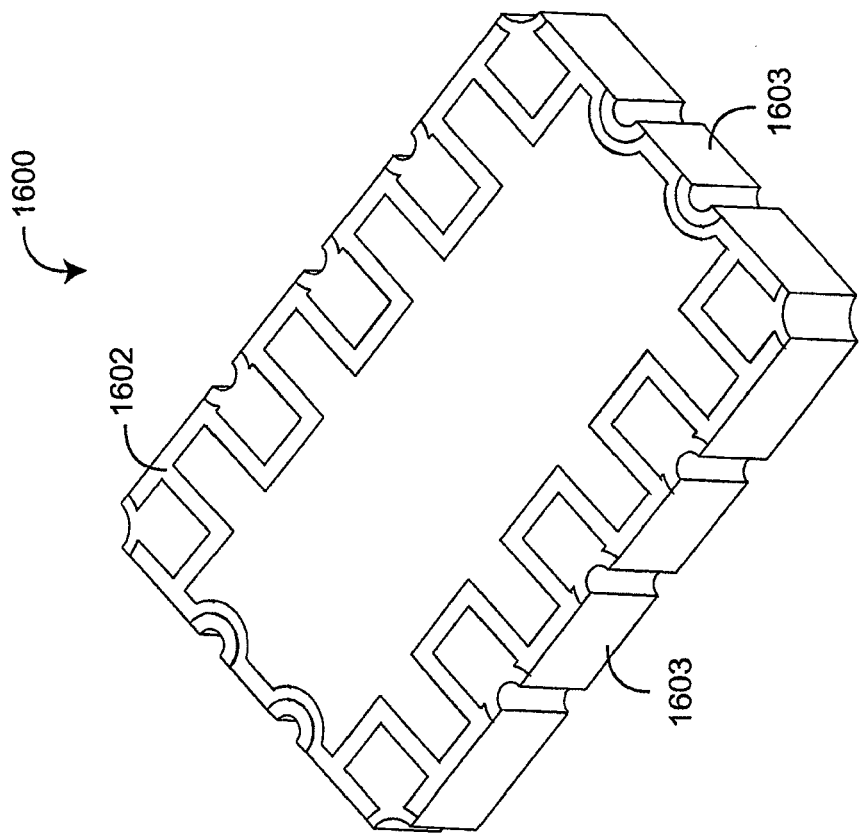
Figure 16E:
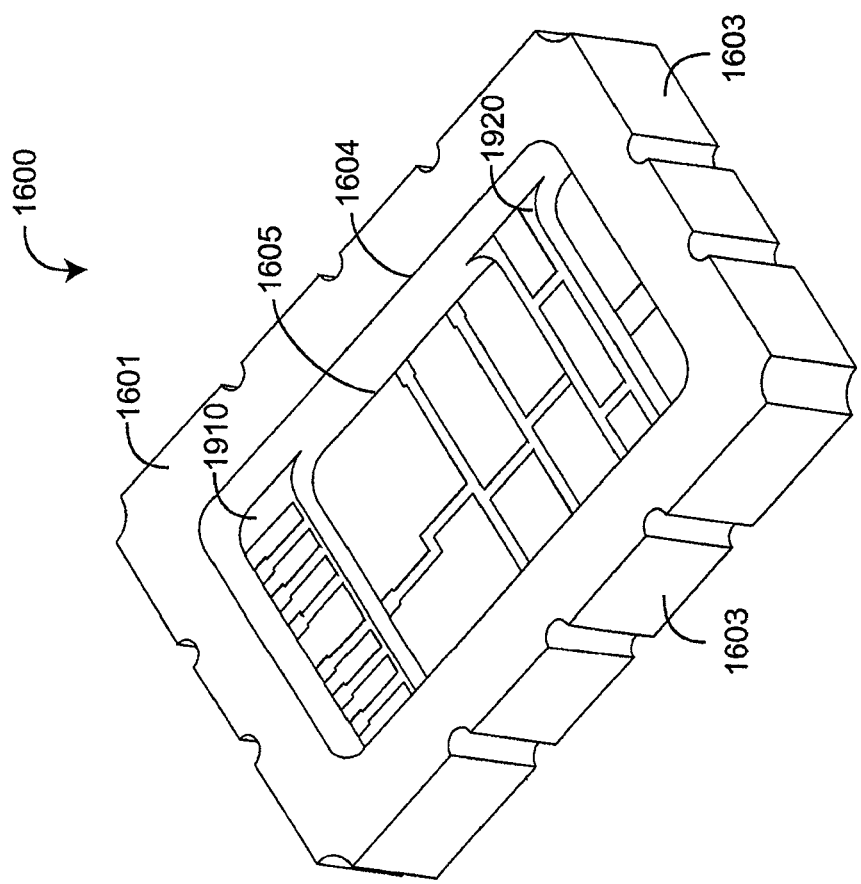
Figure 17:
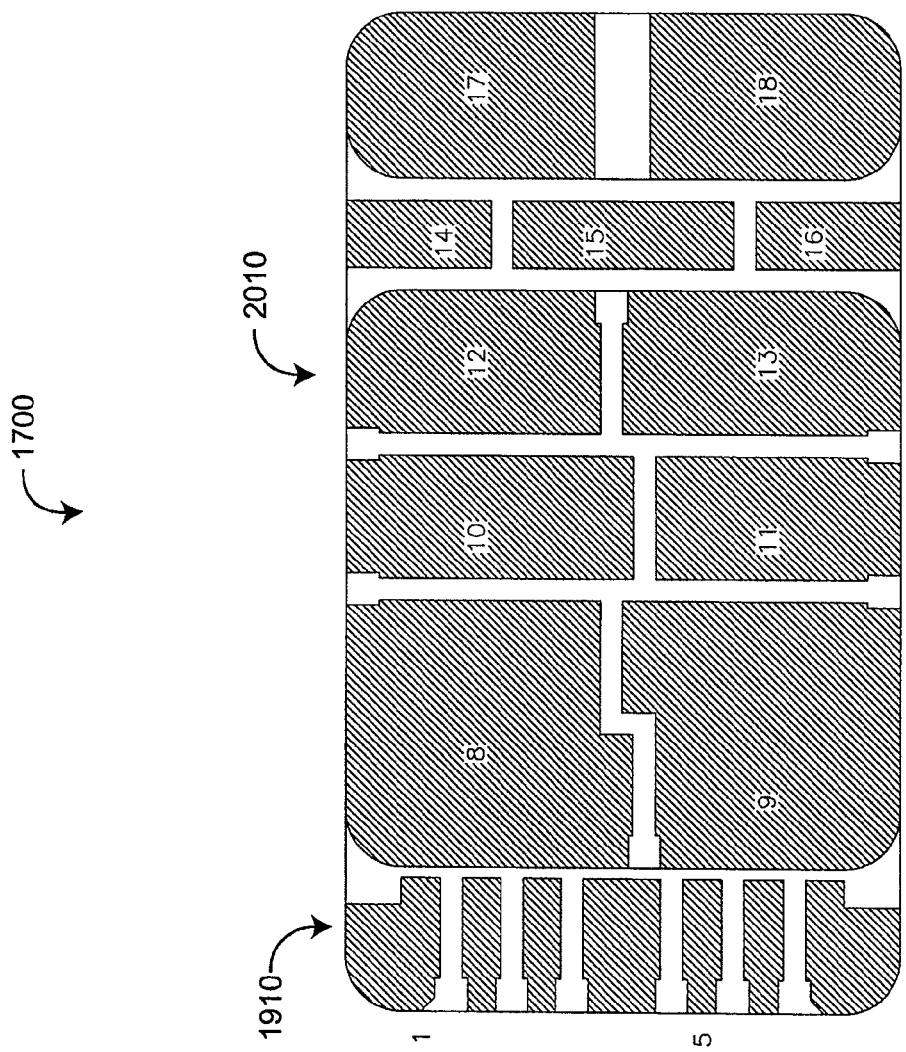

FIG. 17 illustrates upper 1910 and lower 2010 bonding pads. The lower bonding pads 2010, labeled 8 through 16, mount and electrically connect a first side (anode or cathode) of the LEDs 510 (FIG. 5A) into an emitter array. Upper bonding pads 1910, labeled 1 through 7, electrically connect a second side (cathode or anode) of the LEDs 510 (FIG. 5A) into the emitter array, via bonding wires 530 (FIG. 5B). A thermistor 520 (FIG. 5A) is mounted to bonding pads 2010 labeled 17 and 18. Plated "feed-thru" holes and other vias electrically connect the bonding pads 1910, 2010 on the top side 1601 (FIG. 16A) with the solder pads 2220 (FIG. 16C) on the bottom side 1602 (FIG. 16C). In one embodiment, top-side 1601 (FIG. 16A) bonding pad numbers and corresponding bottom-side 1602 (FIG. 16C) solder pad numbers are electrically connected as shown in TABLE 2.

TABLE 2

Connection Table

| BOND PAD NO. | SOLDER PAD NO. |
|---|---|
| 1 | 10 |
| 7 | 13 |
| 11 | 14 |
| 2 | 1 |
| 6 | |
| 12 | |
| 3 | 12 |
| 5 | |
| 13 | |
| 4 | 3 |
| 10 | |
| 8 | 4 |
| 9 | 2 |
| 14 | 5 |
| 16 | 6 |
| | 7 |
| 15 | 11 |
| 17 | 9 |
| 18 | 8 |

Figure 18:
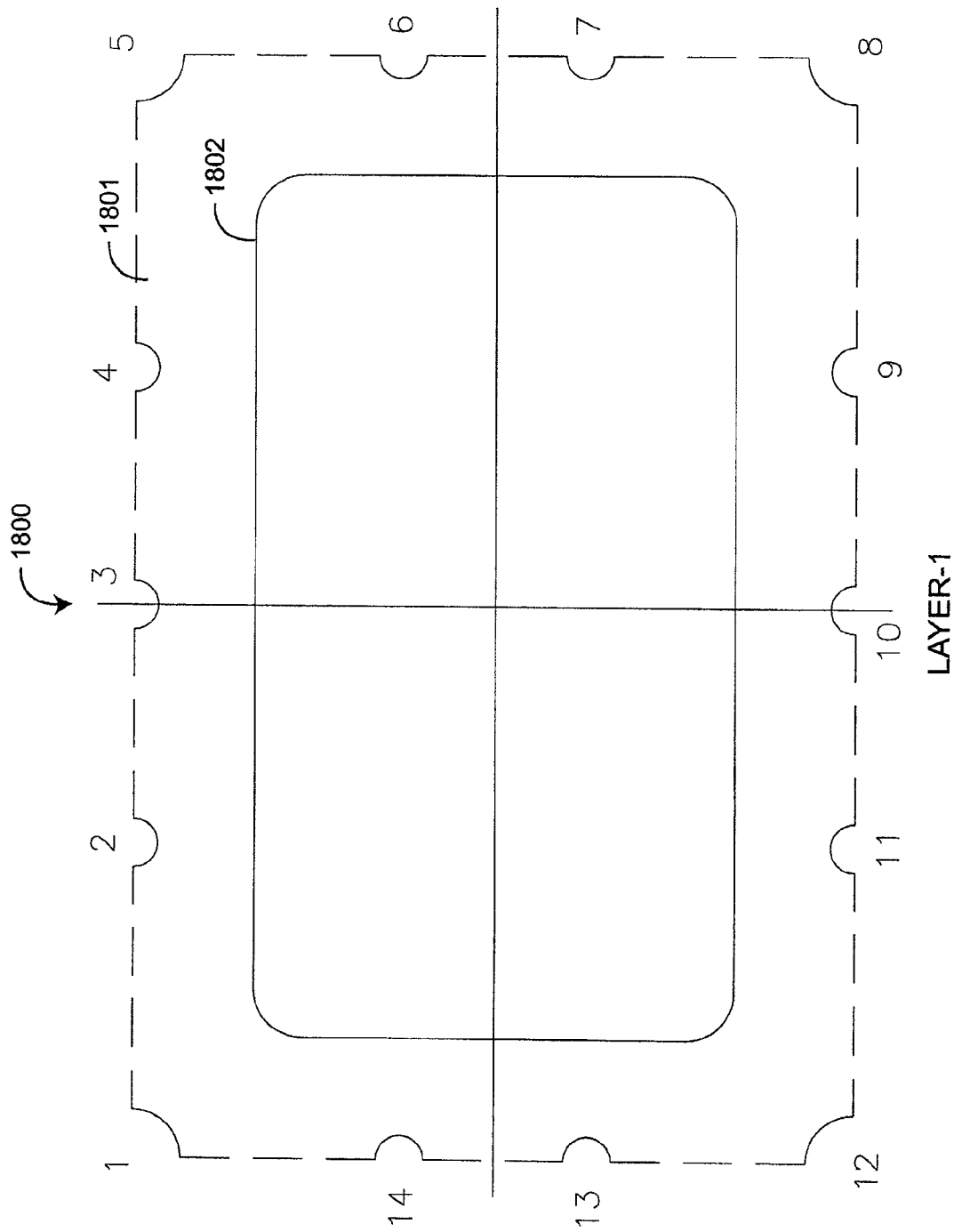

FIG. 18 illustrates a first layer 1800 defining the ceramic substrate top side 1601 (FIG. 16A). The first layer 1800 has a generally rectangular ceramic body 1801 defining a generally rectangular cavity 1802.

Figure 19:
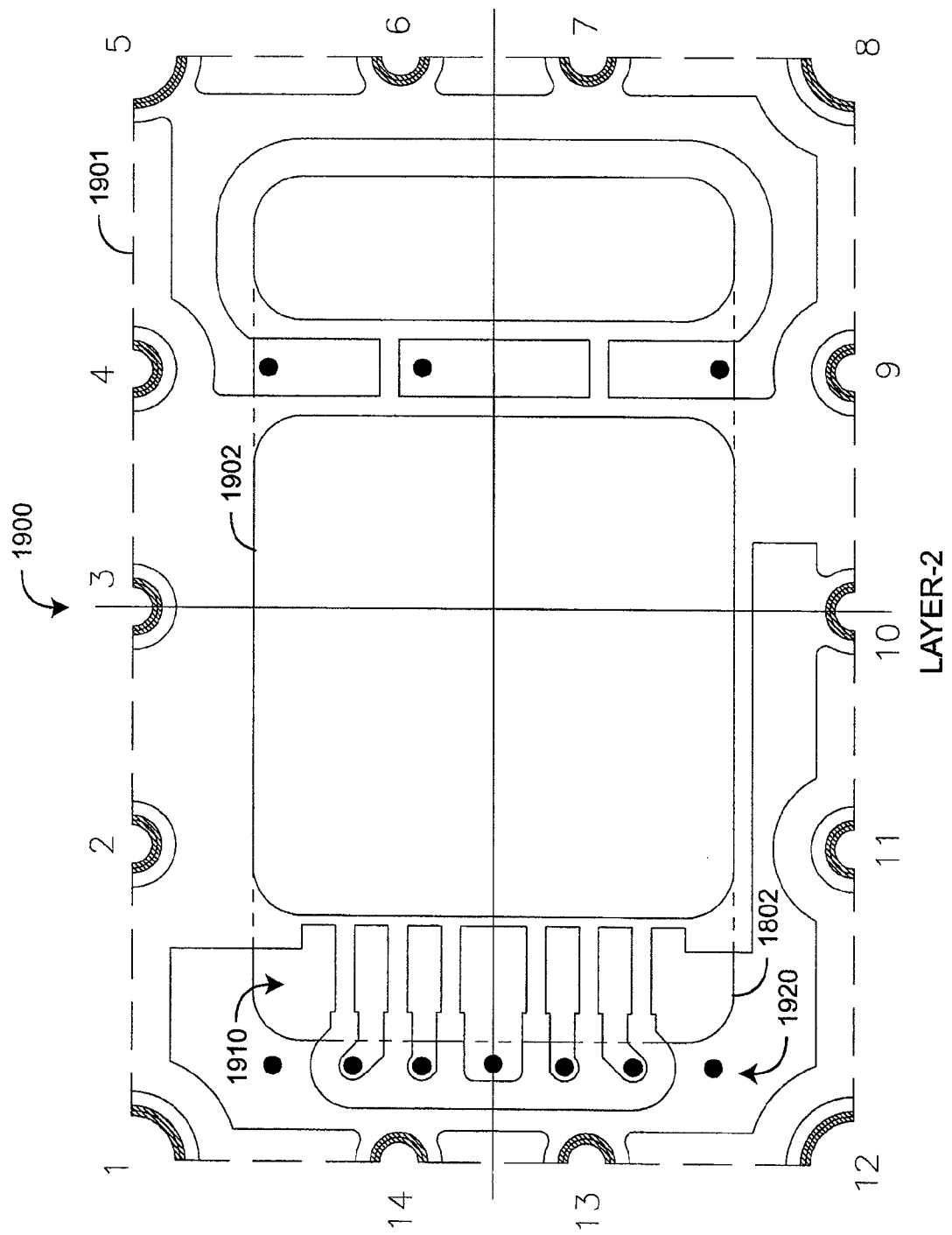

FIG. 19 illustrates a ceramic substrate second layer 1900 proximate the first layer 1800 (FIG. 18). The second layer 1900 has a generally rectangular body 1901 having an outer perimeter coextensive with that of the first layer 1801 (FIG. 18). The body 1901 defines a generally rectangular cavity 1902 having a length less than that of the first layer cavity 1802, so as to form a shelf for the upper bonding pads 1910. The first layer body 1801 (FIG. 18) extends over traces and vias 1920 extending from the upper bonding pads 1910.

Figure 20:
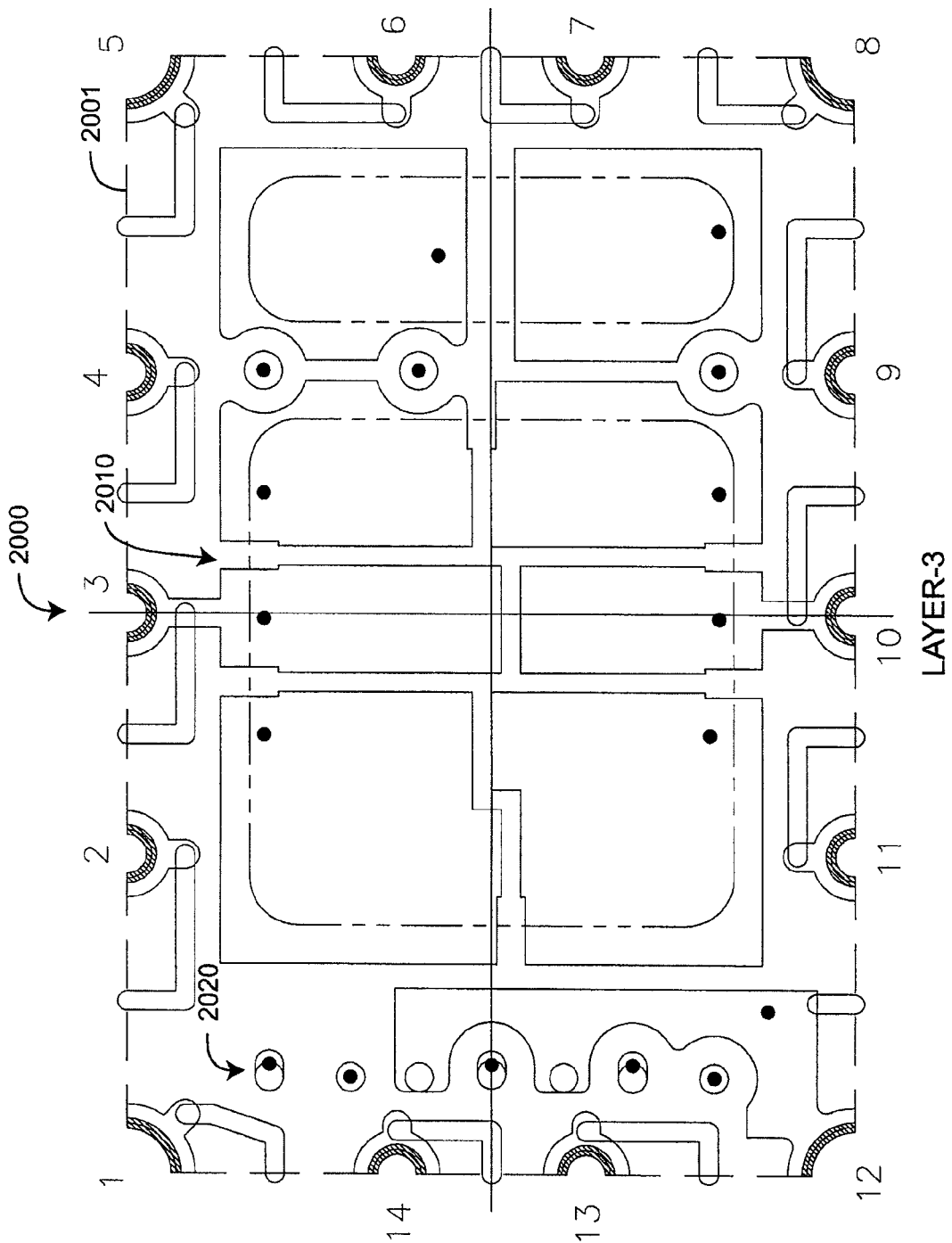

FIG. 20 illustrates a ceramic substrate third layer 2000 proximate the second layer 1900 (FIG. 19). The third layer 2000 has a generally rectangular body 2001 having an outer perimeter coextensive with that of the first layer 1801 (FIG. 18) and second layer 1901 (FIG. 19). Lower bonding pads 2010 are disposed on a top surface of the third layer 2000 proximate the ceramic substrate top side 1601 (FIG. 16A) and distal the ceramic substrate bottom side 1602 (FIG. 16C). The bonding pads 2010 are at least substantially exposed through the first and second layer cavities 1802, 1902 (FIGS. 18-19). Traces and vias 2020 are also disposed on a top surface of the third layer 2000 so as to be covered by the second layer body 1901.

Figure 21:
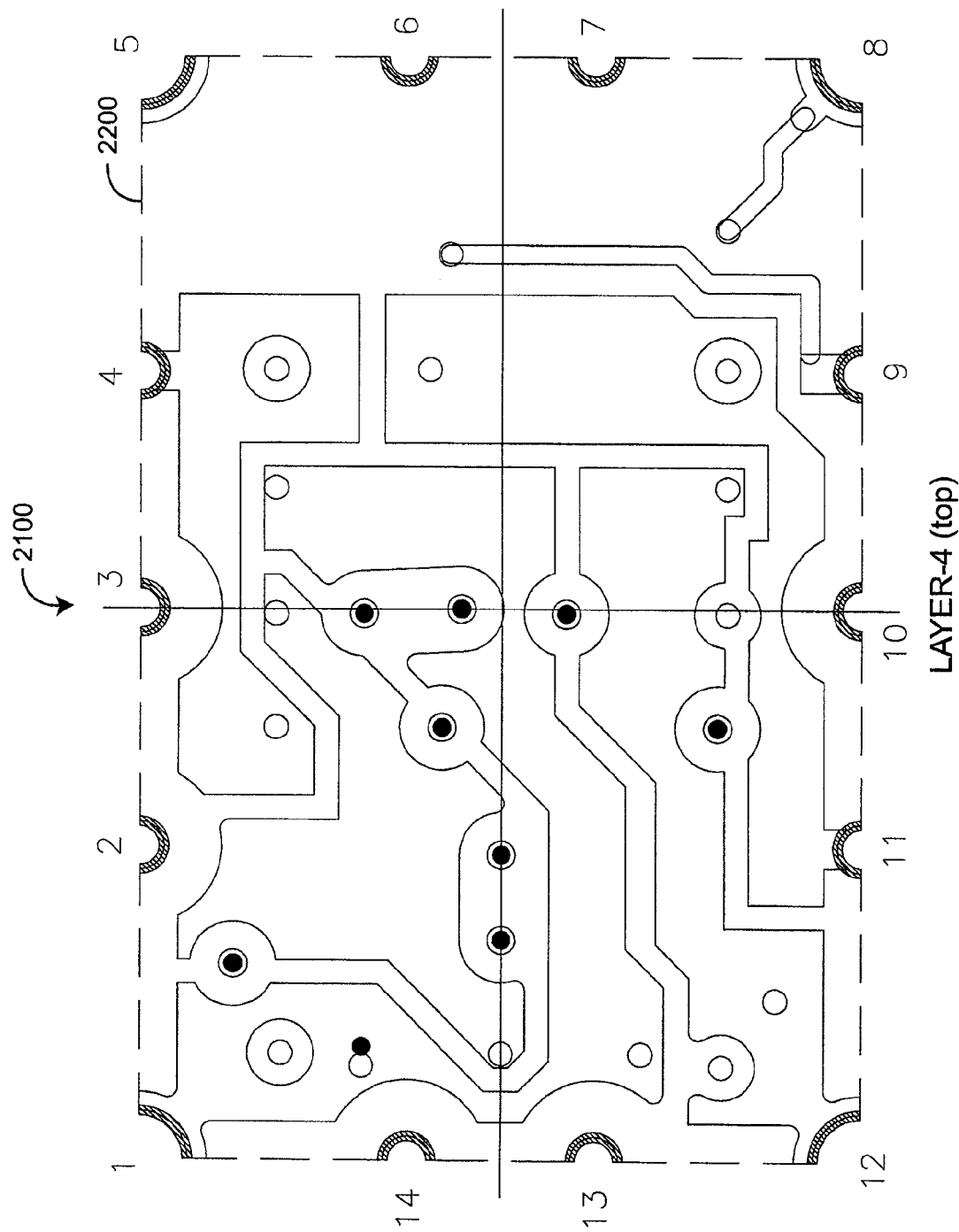

FIG. 21 illustrates traces and vias 2100 disposed on a top side of a fourth layer 1200 proximate the ceramic substrate top side 1601 (FIG. 16A) and distal the ceramic substrate bottom side 1602 (FIG. 16C). The traces and vias 2100 are wholly covered by the third layer body 2001.

Figure 22:
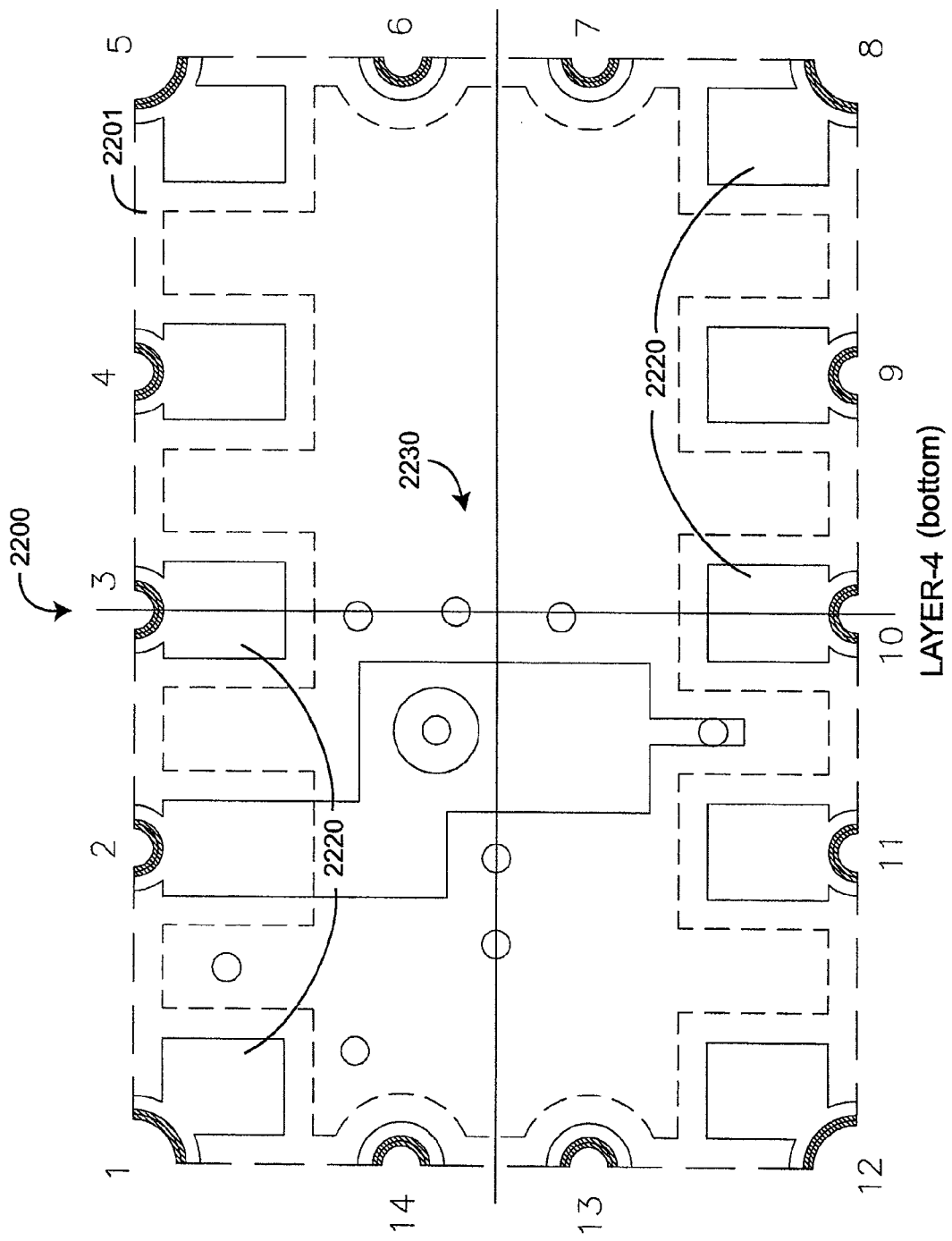
Figure 23:
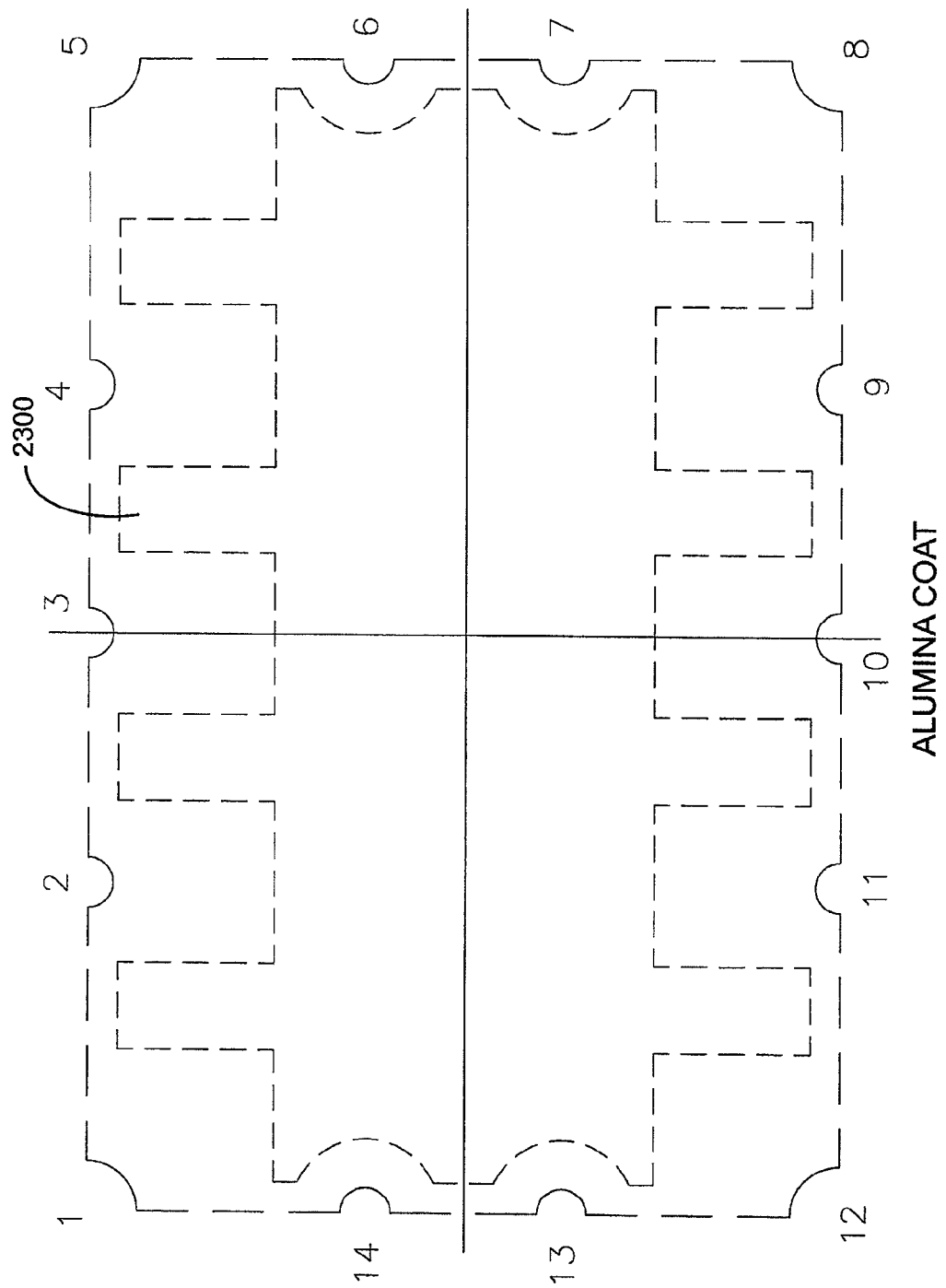

FIG. 22 illustrates a ceramic substrate fourth layer 2200 proximate the third layer 2000 (FIG. 20). The fourth layer 2200 has a generally rectangular body 2201 having an outer perimeter coextensive with that of the first through third layers 1801, 1901, 2001 (FIGS. 18-20). Solder pads 2220 and traces and vias 2230 are disposed on a bottom side of the fourth layer 2200, which is the ceramic substrate bottom side 1602 (FIG. 16C). In an embodiment, an alumina coat 2300 (FIG. 23) extends over at least a substantial portion of the bottom side 1602 (FIG. 16C) so as to coat the traces and vias 2230 and leave exposed the solder pads 2220.

In an embodiment, the ceramic substrate is fabricated from a standard "green" ceramic paste with a dark additive. The resulting "black" ceramic material serves the purpose of preventing light leakage through the edges and bottom of the ceramic substrate.

A ceramic emitter substrate has been disclosed in detail in connection with various embodiments. These embodiments are disclosed by way of examples only and are not to limit the scope of the claims that follow. One of ordinary skill in art will appreciate many variations and modifications.

What is claimed is:

1. An optical medical device that transmits optical radiation into a fleshy tissue site, the optical radiation detected after absorption by pulsatile blood flow within the fleshy tissue site so as to compute constituents of the pulsatile blood flow, the optical medical device comprising:
    a multi-layer generally rectangular-cross-sectioned ceramic body having a top side, a bottom side and an edge adjoining the sides, the ceramic body forming an emitter package different and separate from any detector package configured to output signals indicative of said absorption;
    a cavity defined by an outer periphery of the ceramic body disposed on the top side;
    a plurality of conductive bonding pads disposed within the cavity;
    a plurality of conductive solder pads disposed on the bottom side proximate the edge; and
    a plurality of conductive traces and a plurality of conductive vias forming an interconnect of the bonding pads and the solder pads so that light emitting diodes (LEDs) can be attached to the bonding pads and individually activated as an emitter array via row and column drive signals applied to the solder pads in order to transmit optical radiation out of the cavity.

2. The optical medical device according to claim 1 wherein the multi-layers of the ceramic body comprises:
    a first ceramic layer defining the top side and the cavity;
    a ceramic second layer underlying the first layer;
    a first portion of the bonding pads disposed on the second layer;
    a ceramic third layer underlying the second layer;
    a second portion of the bonding pads disposed on the third layer; and
    a ceramic fourth layer underlying the third layer and defining the bottom side.

3. The optical medical device according to claim 2 further comprising:
    a plurality of LEDs mounted to the bonding pads disposed on the third layer; and
    the LEDs wire bonded to the bonding pads disposed on the second layer.

4. The optical medical device according to claim 1 further comprising:
    an encapsulant disposed within the cavity over at least a portion of the LEDs; and
    the encapsulant functioning as at least one of an optical filter and an optical diffuser.

5. The optical medical device according to claim 4 wherein the ceramic body is constructed of a substantially light absorbing material so as to substantially block LED emitted optical radiation from being transmitted through the ceramic body.

6. A ceramic emitter substrate comprising:
    a ceramic body having a top side, an opposite bottom side and an edge disposed between and along the periphery of the top and bottom sides;
    the ceramic body having a first ceramic layer corresponding to the top side, a second ceramic layer adjacent the first layer, a third ceramic layer adjacent the second layer and a fourth ceramic layer corresponding to the bottom side;
    a cavity defined by the first layer;
    a plurality of solder pads disposed on the fourth layer on the bottom side proximate the edge;
    a plurality of bonding pads disposed on the second layer and on the third layer accessible via the cavity; and
    a plurality of traces disposed on the second, third and fourth layers and vias disposed between the second, third and fourth layers so as to interconnect the solder pads and the bonding pads.

7. A ceramic emitter substrate comprising:
    a ceramic body having a top side, an opposite bottom side and an edge disposed between and along the periphery of the top and bottom sides;
    the ceramic body having a first layer corresponding to the top side, a second layer adjacent the first layer, a third layer adjacent the second layer and a fourth layer corresponding to the bottom side;
    a cavity defined by the first layer;
    a plurality of solder pads disposed on the fourth layer on the bottom side proximate the edge;
    a plurality of bonding pads disposed on the second layer and on the third layer accessible via the cavity;
a plurality of traces disposed on the second, third and fourth layers and vias disposed between the second, third and fourth layers so as to interconnect the solder pads and the bonding pads, wherein the resistance of any one of the traces is less than about 290 milliohms, wherein:
    the ceramic body measures about 0.23×0.15×0.04 inches; and
    the cavity measures about 0.18×0.10 inches.

8. The optical medical device according to claim 7 wherein the ceramic body comprises a dark material that substantially absorbs light transmitted from the light emitting diodes so as to substantially block optical leakage through the ceramic body edge and bottom side.

* * * * *